(12) United States Patent
Solsberg et al.

(10) Patent No.: US 7,942,830 B2
(45) Date of Patent: May 17, 2011

(54) IPSILATERAL APPROACH TO MINIMALLY INVASIVE LIGAMENT DECOMPRESSION PROCEDURE

(75) Inventors: Murray David Solsberg, Englewood, CO (US); Donald Schomer, Cherry Hills Village, CO (US); Timothy Marshall Reeves, Sunnyvale, CA (US); Bryce Way, San Jose, CA (US)

(73) Assignee: Vertos Medical, Inc., Aliso Viejo, CA (US)

( * ) Notice: Subject to any disclaimer, the term of this patent is extended or adjusted under 35 U.S.C. 154(b) by 813 days.

(21) Appl. No.: 11/382,349

(22) Filed: May 9, 2006

(65) Prior Publication Data

US 2007/0276390 A1 Nov. 29, 2007

(51) Int. Cl.
*A61B 17/3205* (2006.01)
(52) U.S. Cl. .......................... 600/564; 606/170
(58) Field of Classification Search ........ 81/52; 128/898; 600/458, 567; 606/60, 79, 86 R, 90, 94, 606/96, 99, 102, 104, 109, 114, 159, 167, 606/170, 192, 223–228, 247–279, 323, 564; 660/190
See application file for complete search history.

(56) References Cited

U.S. PATENT DOCUMENTS

| | | | |
|---|---|---|---|
| 1,493,240 A | 5/1924 | Bohn | |
| 3,628,524 A | 12/1971 | Jamshidi | |
| 3,732,858 A | 5/1973 | Banko | |
| 3,893,445 A | 7/1975 | Hofsess | |
| 3,929,123 A | 12/1975 | Jamshidi | |
| 3,945,372 A | 3/1976 | Milan et al. | |
| 4,103,690 A | 8/1978 | Harris | |
| 4,174,715 A | 11/1979 | Hasson | |
| 4,200,111 A | 4/1980 | Harris | |
| 4,201,213 A | 5/1980 | Townsend | |
| 4,283,129 A | 8/1981 | Bennick, Jr. | |
| 4,535,773 A | 8/1985 | Yoon | |
| 4,603,694 A | 8/1986 | Wheeler | |
| 4,682,606 A | 7/1987 | DeCaprio | |
| 4,708,147 A | 11/1987 | Haaga | |
| 4,733,663 A | 3/1988 | Farley | |

(Continued)

FOREIGN PATENT DOCUMENTS

GB 2177307 1/1987

(Continued)

OTHER PUBLICATIONS

International Search Report and Written Opinion for Appl. No. PCT/US2006/030299 dated Aug. 2007 (8 p.).

(Continued)

*Primary Examiner* — Thomas C Barrett
*Assistant Examiner* — Larry E Waggle, Jr.
(74) *Attorney, Agent, or Firm* — Finnegan, Henderson, Farabow, Garrett & Dunner, LLP

(57) ABSTRACT

A method for treating spinal stenosis is disclosed. The method can include generating a view of a portion of the spinal canal and compressing the dural sac by injecting a fluid to form a safety zone and establish a working zone, wherein the safety zone can be between the working zone and the dural sac. The method can also include percutaneously accessing the epidural space on a first side of the median plane, inserting a tissue removal tool into tissue in the working zone on the first side of the median plane, and using the tissue removal tool to percutaneously reduce a stenosis on the first side of the median plane.

19 Claims, 13 Drawing Sheets

U.S. PATENT DOCUMENTS

| | | | |
|---|---|---|---|
| 4,777,948 A | 10/1988 | Wright | |
| 4,801,293 A | 1/1989 | Jackson | |
| 4,811,734 A | 3/1989 | McGurk-Burleson et al. | |
| 4,834,729 A | 5/1989 | Sjostrom | |
| 4,844,064 A | 7/1989 | Thimsen et al. | |
| 4,850,354 A | 7/1989 | McGurk-Burleson et al. | |
| 4,867,157 A | 9/1989 | McGurk-Burleson et al. | |
| 4,931,059 A | 6/1990 | Markham | |
| 4,991,600 A | 2/1991 | Taylor | |
| 4,994,072 A | 2/1991 | Bhate et al. | |
| 5,026,375 A | 6/1991 | Linovitz et al. | |
| 5,026,386 A | 6/1991 | Michelson | |
| 5,040,542 A | 8/1991 | Gray | |
| 5,108,403 A | 4/1992 | Stern | |
| 5,127,916 A | 7/1992 | Spencer et al. | |
| 5,172,702 A | 12/1992 | Leigh et al. | |
| 5,180,393 A | 1/1993 | Commarmond | |
| 5,190,759 A | 3/1993 | Lindblad et al. | |
| 5,215,105 A | 6/1993 | Kizelshteyn et al. | |
| 5,226,910 A | 7/1993 | Kajiyama et al. | |
| 5,269,785 A | 12/1993 | Bonutti | |
| 5,281,230 A | 1/1994 | Heidmueller | |
| 5,290,303 A | 3/1994 | Pingleton et al. | |
| 5,300,045 A | 4/1994 | Plassche, Jr. | |
| 5,320,110 A | 6/1994 | Wang | |
| 5,354,266 A | 10/1994 | Snoke | |
| 5,366,477 A | 11/1994 | Lemarie et al. | |
| 5,373,854 A | 12/1994 | Kolozsi | |
| 5,385,570 A | 1/1995 | Chin et al. | |
| 5,429,136 A | 7/1995 | Milo et al. | |
| 5,429,138 A | 7/1995 | Jamshidi | |
| 5,439,464 A | 8/1995 | Shapiro | |
| 5,451,227 A | 9/1995 | Michaelson | |
| 5,458,112 A | 10/1995 | Weaver | |
| 5,462,062 A | 10/1995 | Rubinstein | |
| 5,496,269 A | 3/1996 | Snoke | |
| 5,514,379 A | 5/1996 | Weissleder et al. | |
| 5,522,825 A | 6/1996 | Kropf et al. | |
| 5,531,749 A | 7/1996 | Michelson | |
| 5,538,008 A | 7/1996 | Crowe | |
| 5,540,693 A | 7/1996 | Fisher | |
| 5,562,102 A | 10/1996 | Taylor | |
| 5,569,258 A | 10/1996 | Gambale | |
| 5,569,284 A | 10/1996 | Young et al. | |
| 5,578,030 A | 11/1996 | Levin | |
| 5,582,618 A | 12/1996 | Chin et al. | |
| 5,595,186 A | 1/1997 | Rubinstein et al. | |
| 5,613,972 A | 3/1997 | Lee et al. | |
| 5,638,827 A | 6/1997 | Palmer et al. | |
| 5,645,075 A | 7/1997 | Palmer et al. | |
| 5,649,547 A | 7/1997 | Ritchart et al. | |
| 5,681,337 A | 10/1997 | Bray Jr. | |
| 5,705,485 A | 1/1998 | Cini et al. | |
| 5,709,697 A | 1/1998 | Ratcliff et al. | |
| 5,718,237 A | 2/1998 | Haaga | |
| 5,730,754 A | 3/1998 | Obenchain | |
| 5,735,865 A | 4/1998 | Schaumann et al. | |
| 5,759,185 A | 6/1998 | Grinberg et al. | |
| 5,772,597 A | 6/1998 | Goldberger et al. | |
| 5,775,333 A | 7/1998 | Burbank et al. | |
| 5,782,849 A | 7/1998 | Miller | |
| 5,792,044 A * | 8/1998 | Foley et al. | 600/114 |
| 5,797,936 A | 8/1998 | Kleihues | |
| 5,797,939 A | 8/1998 | Yoon | |
| 5,797,958 A | 8/1998 | Yoon | |
| 5,823,970 A | 10/1998 | Terwilliger | |
| 5,827,289 A | 10/1998 | Reiley et al. | |
| 5,827,305 A | 10/1998 | Gordon | |
| 5,836,948 A | 11/1998 | Zucherman et al. | |
| 5,840,338 A | 11/1998 | Roos et al. | |
| 5,843,121 A | 12/1998 | Yoon | |
| 5,853,366 A | 12/1998 | Dowlatshahi | |
| 5,857,996 A | 1/1999 | Snoke | |
| 5,860,991 A | 1/1999 | Klein et al. | |
| 5,868,745 A | 2/1999 | Alleyne | |
| 5,871,453 A | 2/1999 | Banik et al. | |
| 5,873,886 A | 2/1999 | Larsen et al. | |
| 5,879,353 A | 3/1999 | Terry | |
| 5,879,365 A | 3/1999 | Whitfield et al. | |
| 5,916,858 A | 6/1999 | Kim et al. | |
| 5,925,050 A | 7/1999 | Howard, III | |
| 5,925,056 A | 7/1999 | Thomas et al. | |
| 5,931,855 A | 8/1999 | Buncke | |
| 5,954,739 A | 9/1999 | Bonutti | |
| 5,964,782 A | 10/1999 | Lafontaine et al. | |
| 5,980,525 A | 11/1999 | Bryant et al. | |
| 5,985,320 A | 11/1999 | Edwards et al. | |
| 6,010,493 A | 1/2000 | Snoke | |
| 6,019,765 A | 2/2000 | Thornhill et al. | |
| 6,022,362 A | 2/2000 | Lee et al. | |
| 6,053,877 A | 4/2000 | Banik et al. | |
| 6,083,237 A | 7/2000 | Huitema et al. | |
| 6,096,053 A | 8/2000 | Bates | |
| 6,110,127 A | 8/2000 | Suzuki | |
| 6,142,957 A | 11/2000 | Diamond et al. | |
| 6,142,997 A | 11/2000 | Michelson | |
| 6,214,010 B1 | 4/2001 | Farley et al. | |
| 6,221,006 B1 | 4/2001 | Dubrul et al. | |
| 6,241,747 B1 | 6/2001 | Ruff | |
| 6,258,093 B1 | 7/2001 | Edwards et al. | |
| 6,261,294 B1 | 7/2001 | Stihl et al. | |
| 6,261,582 B1 | 7/2001 | Needham et al. | |
| 6,264,087 B1 | 7/2001 | Whitman | |
| 6,264,617 B1 | 7/2001 | Bales et al. | |
| 6,268,405 B1 | 7/2001 | Yao et al. | |
| 6,273,862 B1 | 8/2001 | Privitera et al. | |
| 6,287,304 B1 | 9/2001 | Eggers et al. | |
| 6,296,639 B1 | 10/2001 | Truckai et al. | |
| 6,306,156 B1 | 10/2001 | Clark | |
| 6,332,886 B1 | 12/2001 | Green et al. | |
| 6,358,217 B1 | 3/2002 | Bourassa | |
| 6,358,254 B1 | 3/2002 | Anderson | |
| 6,371,968 B1 | 4/2002 | Kogasaka et al. | |
| 6,375,659 B1 | 4/2002 | Erbe et al. | |
| 6,419,684 B1 | 7/2002 | Heisler et al. | |
| 6,423,332 B1 | 7/2002 | Huxel et al. | |
| 6,425,859 B1 | 7/2002 | Foley et al. | |
| 6,428,486 B2 | 8/2002 | Ritchart et al. | |
| 6,428,498 B2 | 8/2002 | Uflacker | |
| 6,443,910 B1 | 9/2002 | Krueger et al. | |
| 6,454,767 B2 | 9/2002 | Alleyne | |
| 6,464,682 B1 | 10/2002 | Snoke | |
| 6,470,209 B2 | 10/2002 | Snoke | |
| 6,478,805 B1 | 11/2002 | Marino et al. | |
| 6,488,636 B2 | 12/2002 | Bryan et al. | |
| 6,506,190 B1 | 1/2003 | Walshe | |
| 6,514,256 B2 | 2/2003 | Zucherman et al. | |
| 6,520,907 B1 | 2/2003 | Foley et al. | |
| 6,530,933 B1 | 3/2003 | Yeung et al. | |
| 6,533,795 B1 | 3/2003 | Tran et al. | |
| 6,572,563 B2 | 6/2003 | Ouchi | |
| 6,575,919 B1 | 6/2003 | Reiley et al. | |
| 6,575,968 B1 | 6/2003 | Eggers et al. | |
| 6,579,291 B1 * | 6/2003 | Keith et al. | 606/86 A |
| 6,599,310 B2 | 7/2003 | Leung et al. | |
| 6,602,248 B1 | 8/2003 | Sharps et al. | |
| 6,605,294 B2 | 8/2003 | Sawhney | |
| 6,620,185 B1 | 9/2003 | Harvie et al. | |
| 6,626,916 B1 | 9/2003 | Yeung et al. | |
| 6,632,182 B1 | 10/2003 | Treat | |
| 6,645,213 B2 | 11/2003 | Sand et al. | |
| 6,652,558 B2 | 11/2003 | Patel et al. | |
| 6,669,729 B2 | 12/2003 | Chin | |
| 6,682,535 B2 * | 1/2004 | Hoogland | 606/80 |
| 6,692,445 B2 | 2/2004 | Roberts et al. | |
| 6,716,216 B1 | 4/2004 | Boucher et al. | |
| 6,746,093 B2 | 6/2004 | Martinez et al. | |
| 6,746,451 B2 | 6/2004 | Middleton et al. | |
| 6,772,012 B2 | 8/2004 | Ricart et al. | |
| 6,783,534 B2 | 8/2004 | Mehdizadeh | |
| 6,818,001 B2 | 11/2004 | Wulfman et al. | |
| 6,852,095 B1 | 2/2005 | Ray | |
| 6,858,229 B1 | 2/2005 | Hubbell et al. | |
| 6,925,323 B2 | 8/2005 | Snoke | |
| 7,008,433 B2 | 3/2006 | Voellmicke et al. | |
| 7,025,771 B2 | 4/2006 | Kuslich et al. | |
| 7,041,050 B1 | 5/2006 | Ronald | |

| | | |
|---|---|---|
| 7,066,942 B2 | 6/2006 | Treace |
| 7,070,596 B1 | 7/2006 | Woloszko et al. |
| 7,101,382 B2 | 9/2006 | George et al. |
| 7,104,986 B2* | 9/2006 | Hovda et al. ............... 606/32 |
| 7,118,576 B2* | 10/2006 | Gitis et al. ............... 606/87 |
| 7,131,951 B2 | 11/2006 | Angel |
| 7,137,956 B2 | 11/2006 | Nishtalas et al. |
| 7,181,289 B2 | 2/2007 | Pflueger et al. |
| 7,189,206 B2 | 3/2007 | Quick et al. |
| 7,189,240 B1* | 3/2007 | Dekel ............... 606/85 |
| 7,201,722 B2 | 4/2007 | Krueger |
| 7,226,424 B2 | 6/2007 | Ritchart et al. |
| 7,276,032 B2 | 10/2007 | Hibner |
| 7,309,338 B2 | 12/2007 | Cragg |
| 7,322,978 B2 | 1/2008 | West |
| 7,329,402 B2 | 2/2008 | Unger et al. |
| 7,445,634 B2 | 11/2008 | Trieu |
| 2001/0005778 A1 | 6/2001 | Ouchi |
| 2003/0009125 A1 | 1/2003 | Nita et al. |
| 2003/0050574 A1 | 3/2003 | Krueger |
| 2003/0077225 A1 | 4/2003 | Laurent et al. |
| 2003/0165555 A1 | 9/2003 | Ding et al. |
| 2003/0220650 A1 | 11/2003 | Major et al. |
| 2004/0049217 A1 | 3/2004 | Ross et al. |
| 2004/0059370 A1 | 3/2004 | Greene, Jr. et al. |
| 2004/0138701 A1 | 7/2004 | Haluck |
| 2004/0210231 A1 | 10/2004 | Boucher et al. |
| 2005/0037079 A1 | 2/2005 | Son et al. |
| 2005/0038432 A1 | 2/2005 | Shaolian et al. |
| 2005/0070913 A1* | 3/2005 | Milbocker et al. ............... 606/92 |
| 2005/0075630 A1 | 4/2005 | Truckai et al. |
| 2005/0080441 A1 | 4/2005 | Dodge et al. |
| 2005/0137602 A1 | 6/2005 | Assell et al. |
| 2005/0163850 A1 | 7/2005 | Wong et al. |
| 2005/0197661 A1 | 9/2005 | Carrison et al. |
| 2005/0209610 A1 | 9/2005 | Carrison |
| 2005/0228403 A1 | 10/2005 | Ho et al. |
| 2005/0261692 A1* | 11/2005 | Carrison et al. ............... 606/79 |
| 2006/0030785 A1 | 2/2006 | Field et al. |
| 2006/0036211 A1 | 2/2006 | Solsberg et al. |
| 2006/0036271 A1 | 2/2006 | Schomer et al. |
| 2006/0036272 A1* | 2/2006 | Solsberg et al. ............... 606/170 |
| 2006/0089609 A1 | 4/2006 | Bleich et al. |
| 2006/0089633 A1 | 4/2006 | Bleich et al. |
| 2006/0089640 A1 | 4/2006 | Bleich et al. |
| 2006/0094976 A1 | 5/2006 | Bleich |
| 2006/0095028 A1 | 5/2006 | Bleich |
| 2006/0095059 A1* | 5/2006 | Bleich et al. ............... 606/170 |
| 2006/0100651 A1 | 5/2006 | Bleich |
| 2006/0122458 A1 | 6/2006 | Bleich |
| 2006/0122535 A1 | 6/2006 | Daum |
| 2006/0135882 A1* | 6/2006 | Bleich ............... 600/546 |
| 2006/0178682 A1 | 8/2006 | Boehlke |
| 2006/0184175 A1 | 8/2006 | Schomer et al. |
| 2006/0206115 A1 | 9/2006 | Schomer et al. |
| 2006/0224160 A1 | 10/2006 | Trieu et al. |
| 2006/0235334 A1 | 10/2006 | Corvi et al. |
| 2006/0235422 A1 | 10/2006 | Keller |
| 2006/0235451 A1 | 10/2006 | Schomer et al. |
| 2006/0235452 A1 | 10/2006 | Schomer et al. |
| 2006/0264994 A1 | 11/2006 | Schomer et al. |
| 2007/0005084 A1 | 1/2007 | Clague et al. |
| 2007/0027464 A1 | 2/2007 | Way et al. |
| 2007/0055215 A1 | 3/2007 | Tran et al. |
| 2007/0055263 A1 | 3/2007 | Way et al. |
| 2007/0123888 A1 | 5/2007 | Bleich et al. |
| 2007/0123890 A1 | 5/2007 | Way et al. |
| 2007/0162061 A1 | 7/2007 | Way et al. |
| 2007/0198019 A1 | 8/2007 | Schomer et al. |
| 2007/0225703 A1 | 9/2007 | Schmitz et al. |
| 2007/0260253 A1 | 11/2007 | Johnson et al. |
| 2007/0276390 A1 | 11/2007 | Solsberg et al. |
| 2008/0221383 A1 | 9/2008 | Way et al. |
| 2009/0118709 A1 | 5/2009 | Sand et al. |

FOREIGN PATENT DOCUMENTS

| | | |
|---|---|---|
| WO | WO 97/34536 A2 | 9/1997 |
| WO | WO 97/34536 A3 | 11/1997 |
| WO | WO 98/22022 | 5/1998 |
| WO | WO 00/45868 A1 | 8/2000 |
| WO | WO 01/08571 A1 | 2/2001 |
| WO | WO 01/82998 | 11/2001 |
| WO | WO 02/076311 A2 | 10/2002 |
| WO | WO 02/076311 A3 | 10/2002 |
| WO | WO 2006/015302 | 2/2006 |
| WO | WO 2006/044727 | 4/2006 |
| WO | WO 2007/085628 | 8/2007 |
| WO | WO 2007/113808 | 10/2007 |
| WO | WO 2008/042793 | 4/2008 |
| WO | WO 2008/070867 | 6/2008 |
| WO | WO 2008/139260 | 11/2008 |

OTHER PUBLICATIONS

PCT International Search Report and Written Opinion for Appl. No. PCT/US06/04342 dated Sep. 18, 2007 (8 p.).
PCT International Search Report for International Application No. PCT/US05/27216 dated Nov. 29, 2005.
Brunette, J. et al. "Comparative Rheology of Low- and Iso-Osmolarity Contrast Agents at Different Temperatures Catheterization and Cardiovascular Interventions," 71:78-83 (2008).
European Search Report issued in EP 08253596.4, mailed on Mar. 27, 2009.
European Search Report issued in EP 08253854.7, mailed on Apr. 4, 2009.
Great Britain Search Report issued in GB 0821929.7, dated Mar. 2, 2009.
International Search Report and Written Opinion issued in PCT/US2006/30298, mailed on Jan. 11, 2008.
International Search Report and Written Opinion issued in PCT/US2006/30302, mailed on Jul. 3, 2008.
International Search Report and Written Opinion issued in PCT/US2007/68553, mailed on Sep. 11, 2008.
International Search Report issued in PCT/US2008/53681, mailed on Jul. 29, 2008.
Office Action issied in U.S. Appl. No. 10/595,536, mailed on Jul. 9, 2009.
Office Action issued in U.S. Appl. No. 11/555,899, mailed Jul. 8, 2009.
Office Action issued in U.S. Appl. No. 10/595,536, mailed on Jan. 21, 2009.
Office Action issued in U.S. Appl. No. 10/595,536, mailed on May 12, 2008.
Office Action issued in U.S. Appl. No. 11/193,278, mailed on Apr. 22, 2009.
Office Action issued in U.S. Appl. No. 11/193,278, mailed on May 9, 2008.
Office Action issued in U.S. Appl. No. 11/193,278, mailed on Nov. 3, 2008.
Office Action issued in U.S. Appl. No. 11/193,557, mailed on Apr. 28, 2009.
Office Action issued in U.S. Appl. No. 11/193,557, mailed on Nov. 13, 2008.
Office Action issued in U.S. Appl. No. 11/193,559, mailed on Aug. 22, 2008.
Office Action issued in U.S. Appl. No. 11/193,559, mailed on Jun. 24, 2009.
Office Action issued in U.S. Appl. No. 11/193,581, mailed on Jan. 8, 2009.
Office Action issued in U.S. Appl. No. 11/193,581, mailed on Jun. 17, 2009.
Office Action issued in U.S. Appl. No. 11/382,349, mailed on Feb. 27, 2009.
Office Action issued in U.S. Appl. No. 11/461,036, mailed on May 5, 2009.
Office Action issued in U.S. Appl. No. 11/461,045, mailed on Apr. 1, 2009.
Office Action issued in U.S. Appl. No. 11/556,213, mailed Jul. 23, 2009.
Written Opinion issued in PCT/US2005/27216, mailed on Jan. 12, 2006.
European Search Report issued in EP 08729616.6, mailed on Feb. 2, 2010.

Office Action issued in U.S. Appl. No. 11/193,557, mailed Jan. 20, 2010.
Office Action issued in U.S. Appl. No. 11/193,559, mailed on Mar. 18, 2010.
Office Action issued in U.S. Appl. No. 11/193,581, mailed Jan. 5, 2010.
Office Action issued in U.S. Appl. No. 11/380,377, mailed on Jun. 22, 2010.
Office Action issued in U.S. Appl. No. 11/556,213, mailed on Apr. 27, 2010.
Office Action issued in U.S. Appl. No. 11/556,213, mailed on Oct. 28, 2009.
Office Action issued in U.S. Appl. No. 12/188,360, mailed on Mar. 5, 2009.

* cited by examiner

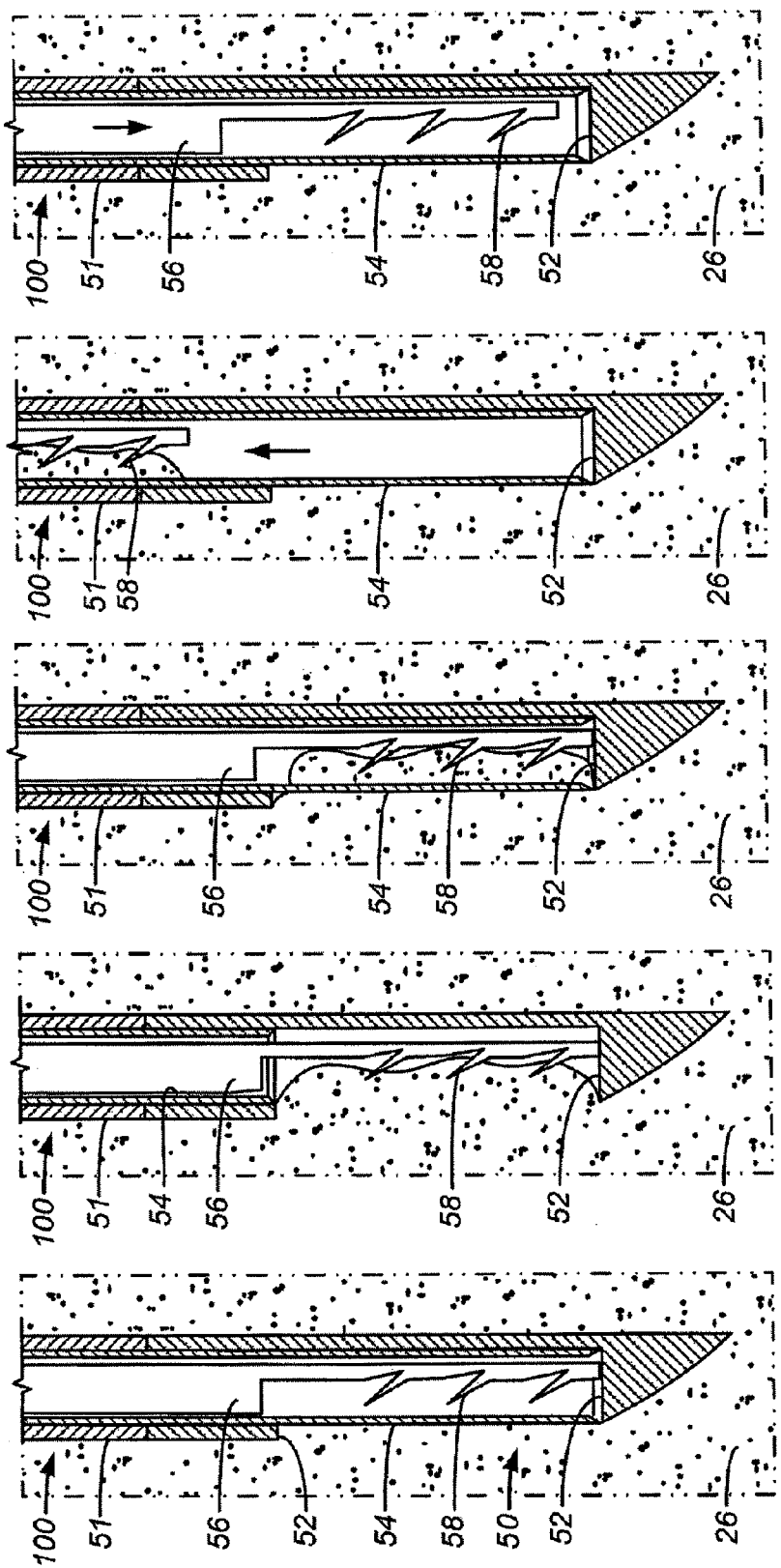

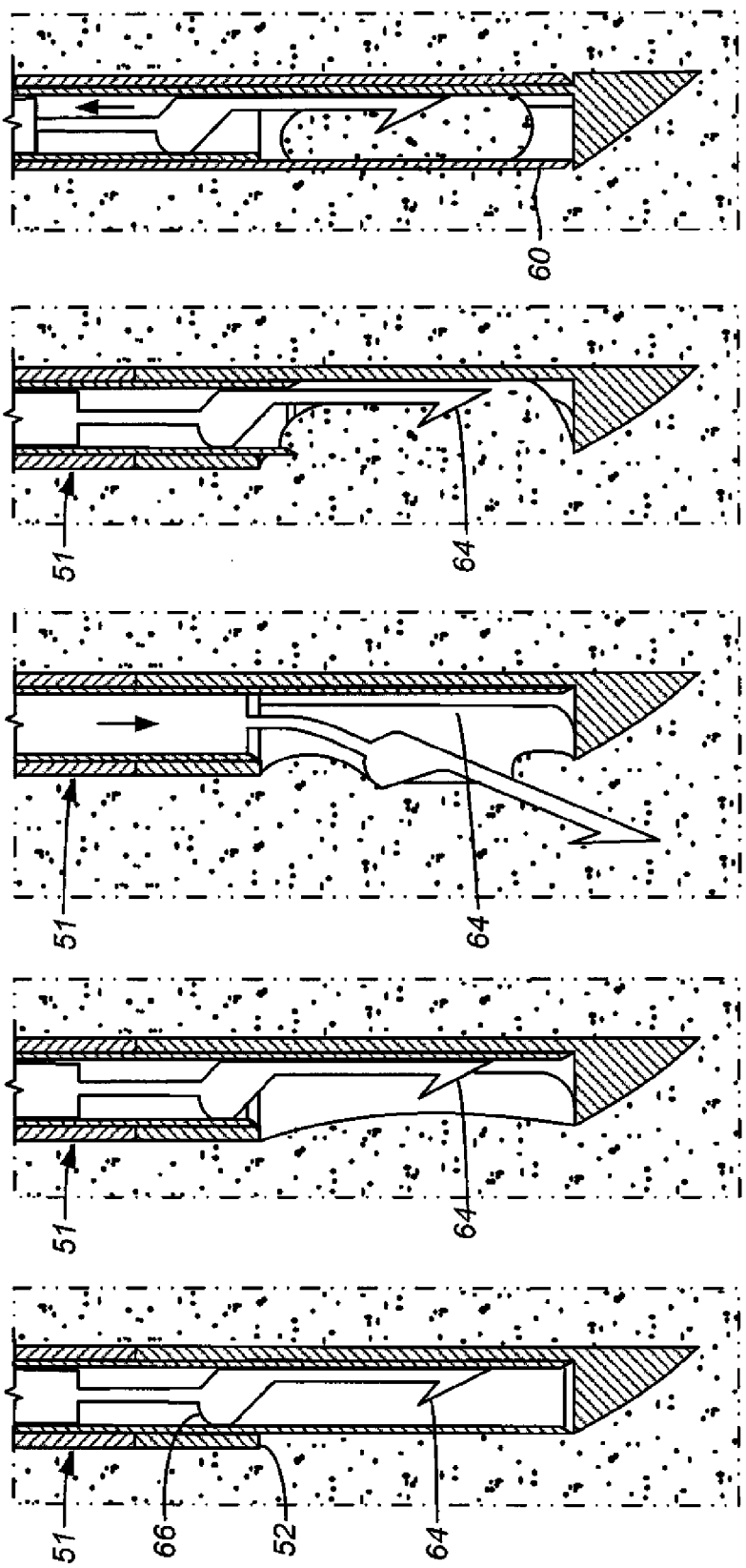

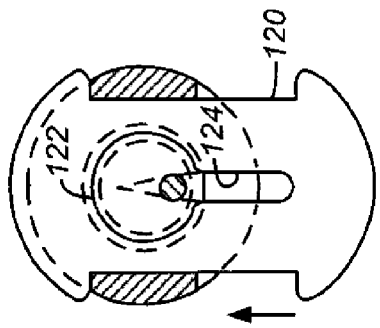
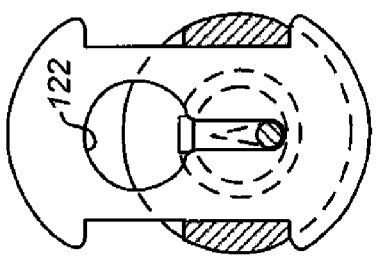
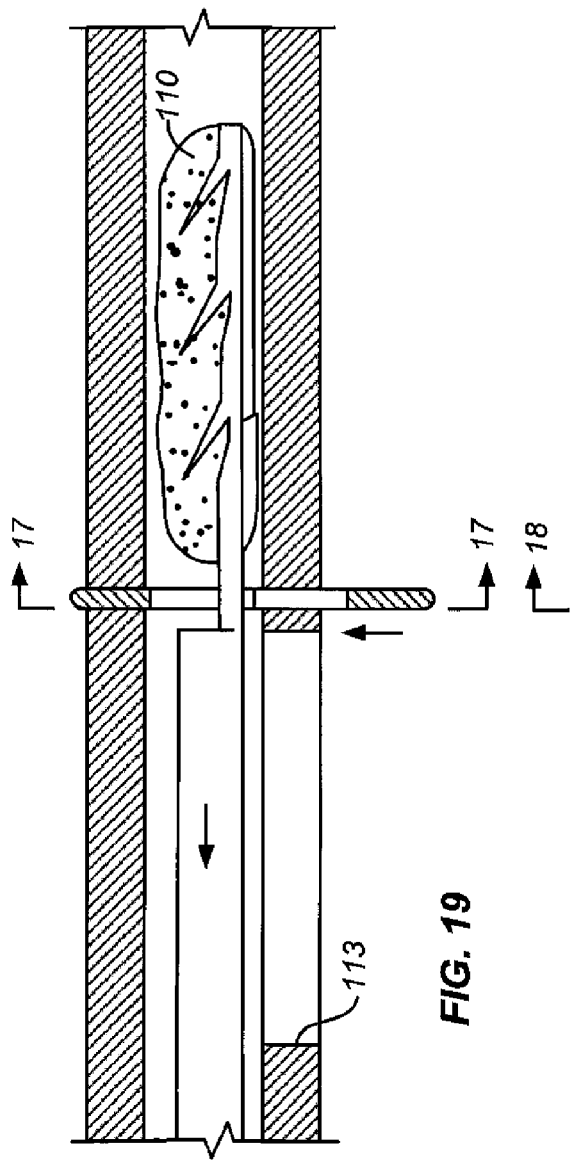
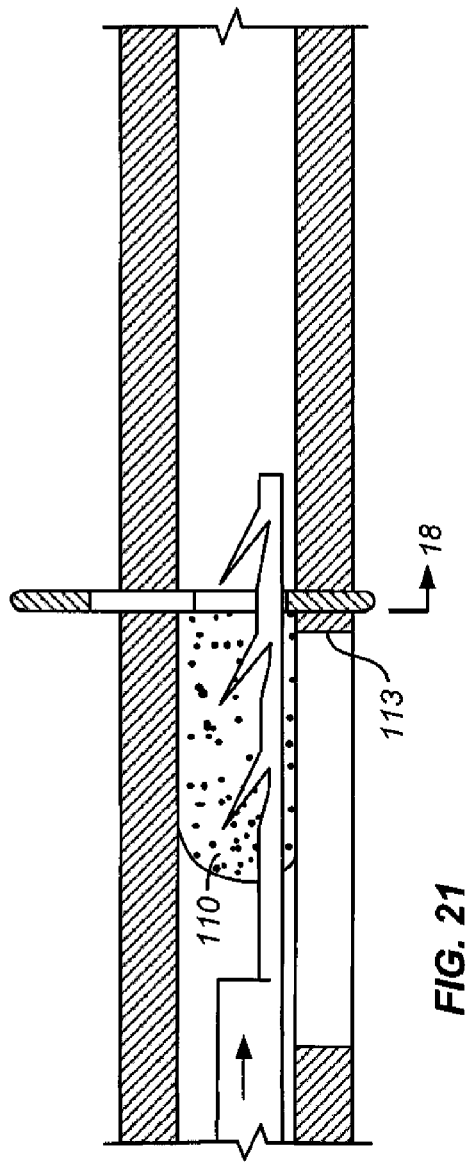
FIG. 19
FIG. 20
FIG. 21
FIG. 22

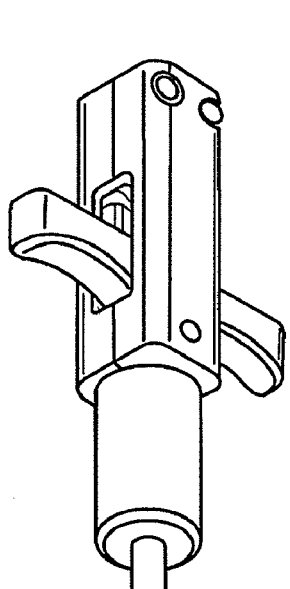
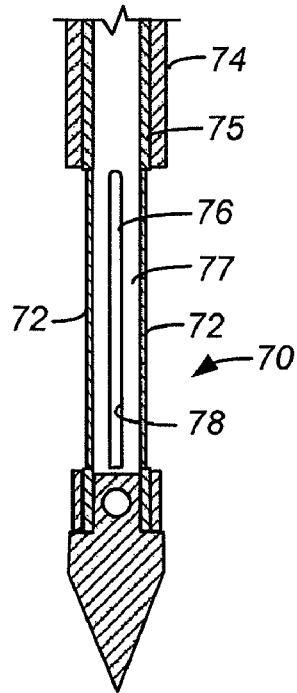
FIG. 26
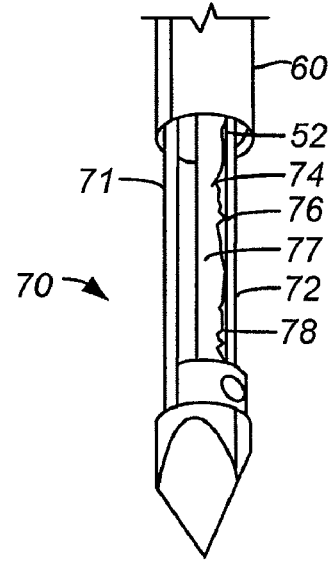
FIG. 27
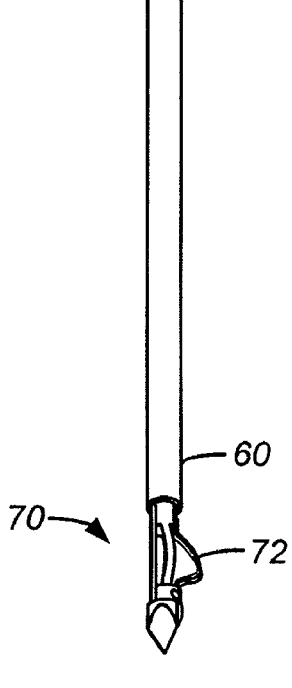
FIG. 25
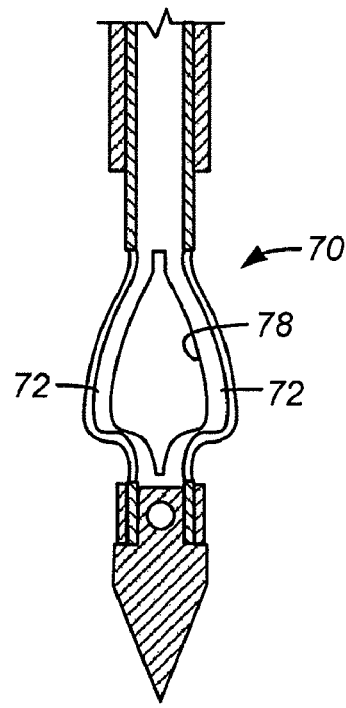
FIG. 28
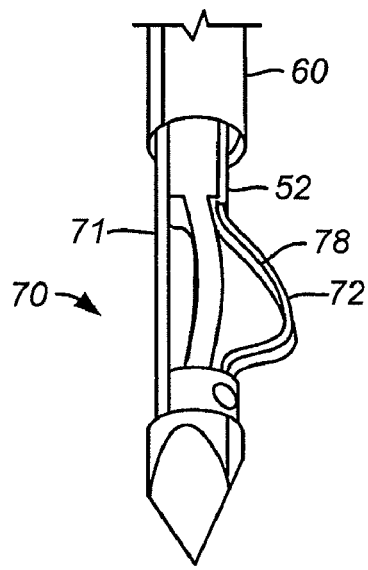
FIG. 29

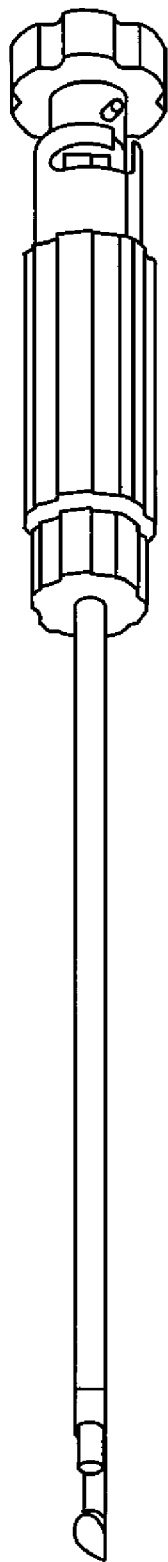 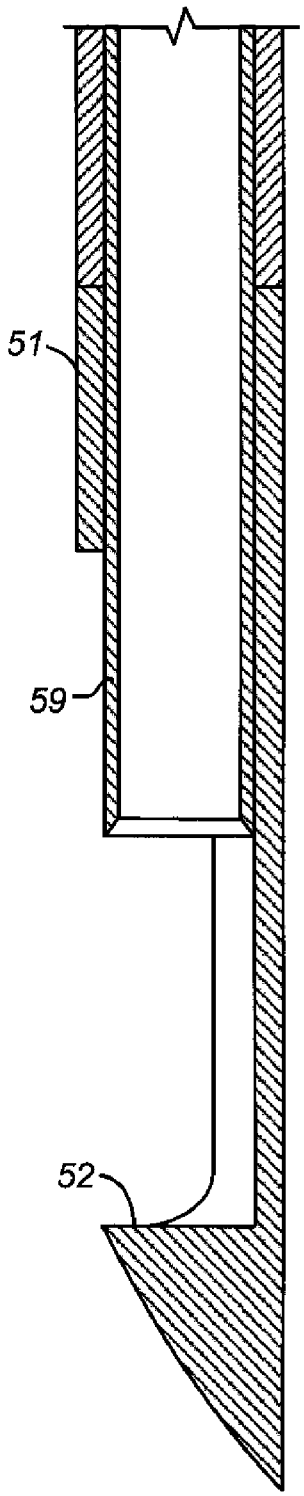 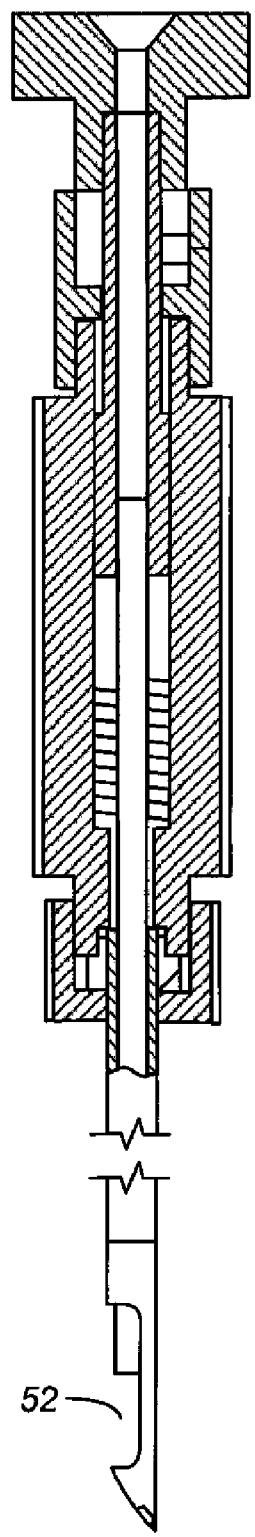
*FIG. 32*  *FIG. 33*  *FIG. 34*

IPSILATERAL APPROACH TO MINIMALLY INVASIVE LIGAMENT DECOMPRESSION PROCEDURE

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND

1. Field of the Invention

The present invention relates to minimally invasive methods, devices and systems for treating spinal disorders using imaging guidance. This invention also relates to devices used to reduce stenosis and increase the cross-sectional area of the spinal canal available for the spinal cord. This invention also relates to methods, devices, therapies and medications used to treat disorders that involve the epidural space within the spinal canal.

2. Background of the Invention

The vertebral column (spine, spinal column, backbone) forms the main part of the axial skeleton, provides a strong yet flexible support for the head and body, and protects the spinal cord disposed in the vertebral canal, which is formed within the vertebral column The vertebral column comprises a stack of vertebrae with an intervertebral disc between adjacent vertebrae. The vertebrae are stabilized by muscles and ligaments that hold the vertebrae in place and limit the movements of the vertebrae.

As illustrated in FIG. 1, each vertebra 10 includes a vertebral body 12 that supports a vertebral arch 14. A median plane 210 generally divides vertebra 10 into two substantially equal lateral sides. Vertical body 12 has the general shape of a short cylinder and is anterior to the vertebral arch 14. The vertebral arch 14 together with vertebral body 12 encloses a space termed the vertebral foramen 15. The succession of vertebral foramen 15 in adjacent vertebrae 10 along the vertebral column define the vertebral canal (spinal canal), which contains the spinal cord.

Vertebral arch 14 is formed by two pedicles 24 which project posteriorly to meet two laminae 16. The two laminae 16 meet posteriomedially to form the spinous process 18. At the junction of pedicles 24 and laminae 16, six processes arise. Two transverse processes 20 project posterolaterally, two superior articular processes 22 project generally superiorly and are positioned superior to two inferior articular processes 25 that generally project inferiorly.

The vertebral foramen 15 is generally an oval shaped space that contains and protects the spinal cord 28 Spinal cord 28 comprises a plurality of nerves 34 surrounded by cerebrospinal fluid (CSF) and an outermost sheath/membrane called the dural sac 32. The CSF filled dural sac 32 containing nerves 34 is relatively compressible. Posterior to the spinal cord 28 within vertebral foramen 15 is the ligamentum flavum 26. Laminae 16 of adjacent vertebral arches 14 in the vertebral column are joined by the relatively broad, elastic ligamentum flavum 26.

In degenerative conditions of the spine, narrowing of the spinal canal (stenosis) can occur. Lumbar spinal stenosis is often defined as a dural sac cross-sectional area less than 100 mm$^2$ or an anterior-posterior (AP) dimension of the canal of less than 10-12 mm for an average male.

The source of many cases of lumbar spinal stenosis is thickening of the ligamentum flavum. Spinal stenosis may also be caused by subluxation, facet joint hypertrophy, osteophyte formation, underdevelopment of spinal canal, spondylosis deformans, degenerative intervertebral discs, degenerative spondylolisthesis, degenerative arthritis, ossification of the vertebral accessory ligaments and the like. A less common cause of spinal stenosis, which usually affects patients with morbid obesity or patients on oral corticosteroids, is excess fat in the epidural space. The excessive epidural fat compresses the dural sac, nerve roots and blood vessels contained therein and resulting in back, leg pain and weakness and numbness of the legs. Spinal stenosis may also affect the cervical and, less commonly, the thoracic spine.

Patients suffering from spinal stenosis are typically first treated with exercise therapy, analgesics, and anti-inflammatory medications. These conservative treatment options frequently fail. If symptoms are severe, surgery is required to decompress the spinal cord and nerve roots.

In some conventional approaches to correct stenosis in the lumbar region, an incision is made in the back and the muscles and supporting structures are stripped away from the spine, exposing the posterior aspect of the vertebral column. The thickened ligamentum flavum is then exposed by removal of a portion of the vertebral arch, often at the laminae, covering the back of the spinal canal (laminectomy). The thickened ligamentum flavum ligament can then be excised by sharp dissection with a scalpel or punching instruments such as a Kerison punch that is used to remove small chips of tissue. The procedure is performed under general anesthesia. Patients are usually admitted to the hospital for approximately five to seven days depending on the age and overall condition of the patient. Patients usually require between six weeks and three months to recover from the procedure. Further, many patients need extended therapy at a rehabilitation facility to regain enough mobility to live independently.

Much of the pain and disability after an open laminectomy results from the tearing and cutting of the back muscles, blood vessels, supporting ligaments, and nerves that occurs during the exposure of the spinal column. Also, because the spine stabilizing back muscles and ligaments are stripped and detached from the spine during the laminectomy, these patients frequently develop spinal instability post-operatively.

Minimally invasive techniques offer the potential for less post-operative pain and faster recovery compared to traditional open surgery. Percutaneous interventional spinal procedures can be performed with local anesthesia, thereby sparing the patient the risks and recovery time required with general anesthesia. In addition, there is less damage to the paraspinal muscles and ligaments with minimally invasive techniques, thereby reducing pain and preserving these important stabilizing structures.

Various techniques for minimally invasive treatment of the spine are known. Microdiscectomy is performed by making a small incision in the skin and deep tissues to create a portal to the spine. A microscope is then used to aid in the dissection of the adjacent structures prior to discectomy. The recovery for this procedure is much shorter than traditional open discectomies. Percutaneous discectomy devices with fluoroscopic guidance have been used successfully to treat disorders of the disc but not to treat spinal stenosis or the ligamentum flavum directly. Arthroscopy or direct visualization of the spinal structures using a catheter or optical system have also been proposed to treat disorders of the spine including spinal stenosis, however these devices still use miniaturized standard surgical instruments and direct visualization of the spine similar to open surgical procedures. These devices and techniques are limited by the small size of the canal and these operations are difficult to perform and master. In addition, these procedures are painful and often require general anesthesia. Further, the arthroscopy procedures are time consuming and the fiber optic systems are expensive to purchase and maintain.

Still further, because the nerves of the spinal cord pass through the spinal canal directly adjacent to and anterior to the ligamentum flavum, any surgery, regardless of whether open or percutaneous, includes a risk of damage to the nerves of the spinal cord.

Hence, it remains desirable to provide simple methods, techniques, and devices for treating spinal stenosis and other spinal disorders without requiring open surgery. It is further desired to provide a system whereby the risk of damage to the dural sac containing the spinal nerves may be reduced.

SUMMARY OF THE INVENTION

The present invention provides methods, devices and systems for treating spinal stenosis or other spinal disorders using image guidance in combination with percutaneous techniques. Embodiments of the present approach are referred to as an ipsilateral approach minimally invasive ligament decompression procedure (ILAMP). In some embodiments, the present invention provides a means for compressing the thecal sac within the epidural space so as to provide a safety zone in which further surgical procedures may be performed without risk of damaging nearby tissues or the thecal sac itself.

In another embodiment, the present invention provides a method for treating stenosis in a spine of a patient. In an embodiment, the method comprises the steps of a) generating at least one view of a portion of the spinal canal in the region of interest; b) percutaneously accessing the epidural space in the region of interest; c) compressing the dural sac in the region of interest by injecting a fluid to form a safety zone and establish a working zone, the safety zone lying between the working zone and the dural sac; d) inserting a tissue removal tool into tissue in the working zone; e) using the tool to percutaneously reduce the stenosis by removing at least a portion of the ligamentum flavum by inserting an excision tool into the ligamentum flavum in the region of interest, wherein the portion of the ligamentum flavum removed is on the same side of the ligamentum flavum where the excision tool is inserted into the ligamentum flavum; and f) utilizing the at least one view to position the tool during at least a part of step d) and at least part of step e).

The foregoing has outlined rather broadly the features and technical advantages of embodiments of the present invention in order that the detailed description that follows may be better understood Additional features and advantages of embodiments of the present invention will be described hereinafter that form the subject of the claims. It should be appreciated by those skilled in the art that the conception and the specific embodiments disclosed may be readily utilized as a basis for modifying or designing other structures for carrying out the same purposes. It should also be realized by those skilled in the art that such equivalent constructions do not depart from and scope of the invention as set forth in the appended claims.

BRIEF DESCRIPTION OF THE DRAWINGS

For a more complete understanding of the invention, reference is made to the accompanying drawings, wherein:

FIGS. 9-13 are a series of illustrations showing tissue excision by a tissue-excision tool constructed in accordance with a first embodiment of the invention;

FIGS. 14-18 are a series of illustrations showing tissue excision by a tissue-excision tool constructed in accordance with a second embodiment of the invention;

FIGS. 19 and 21 are sequential illustrations showing removal of tissue from a tissue-excision tool by a tissue-removal device constructed in accordance with an embodiment of the invention;

FIGS. 20 and 22 are end views of the tissue-removal device of FIGS. 19 and 21, respectively;

FIG. 25 is a perspective view of a tissue-excision tool constructed in accordance with a third embodiment of the invention;

FIGS. 26 and 27 are enlarged cross-sectional and perspective views, respectively, of the grasping device of FIG. 25 in its retracted position;

FIGS. 28 and 29 are enlarged cross-sectional and perspective views, respectively, of the grasping device of FIG. 25 in its extended position;

FIG. 32 is a perspective view of an entire tool constructed in accordance with preferred embodiments;

FIG. 33 is an enlarged cross-sectional view of the distal tip of the tool of FIG. 32 with the aperture partially opened; and FIG. 34 is a cross-sectional view of the handle end of the tool of FIG. 32.

DETAILED DESCRIPTION OF THE PREFERRED EMBODIMENTS

Figure 1:
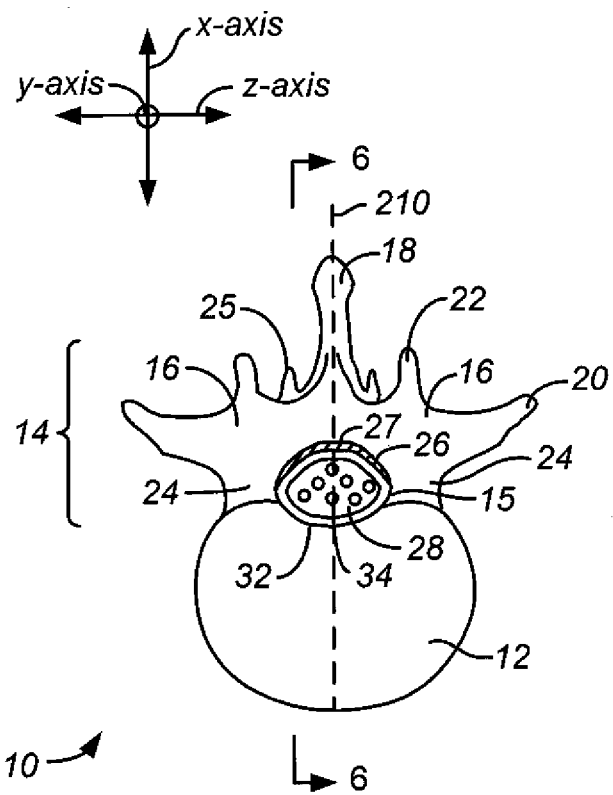
FIG. 1 is cross-section of the spine viewed from the space between two vertebrae, showing the upper surface of one vertebra and the spinal canal with the dural sac and a normal (un-stenosed) ligamentum flavum therein.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment For purposes of this discussion, the x-, y-, and z-axis are shown in FIGS. 1, 3, 5, 6, and 7 to aid in understanding the descriptions that follow. The x-, y-, and z-axis have been assigned as follows. The x-axis is perpendicular to the longitudinal axis of the vertebral column and perpendicular to the coronal/frontal plane (i.e., x-axis defines anterior vs. posterior relationships). The y-axis runs substantially parallel to the vertebral column and perpendicular to the transverse plane (i.e., y-axis defines superior vs. inferior relationships). The z-axis is perpendicular to the longitudinal axis of the vertebral column and perpendicular to the median/midsagittal plane (i.e., z-axis defines the lateral right and left sides of body parts). The set of coordinate axes (x-, y-, and z-axis) are consistently maintained throughout although different views of vertebrae and the spinal column may be presented.

It is to be understood that the median/midsagittal plane passes from the top to the bottom of the body and separates the left and the right sides of the body, and the spine, into substantially equal halves (e.g., two substantially equal lateral sides). Further, it is to be understood that the frontal/coronal plane essentially separates the body into the forward (anterior) half and the back (posterior) half and is perpendicular to the median plane. Still further, it is to be understood that the transverse plane is perpendicular to both the median plane and coronal plane and is the plane which divides the body into an upper and a lower half.

The Spinal Canal and Spinal Stenosis

Referring again to FIG. 1, vertebral foramen 15 contains a portion of the ligamentum flavum 26, spinal cord 28, and an epidural space 27 between ligamentum flavum 26 and spinal cord 28. Spinal cord 28 comprises a plurality of nerves 34 surrounded by cerebrospinal fluid (CSF) contained within dural sac 32 Nerves 34 normally comprise only a small proportion of the dural sac 32 volume. Thus, CSF filled dural sac 32 is somewhat locally compressible, as localized pressure causes the CSF to flow to adjacent portions of the dural sac. Epidural space 27 is typically filled with blood vessels and fat. The posterior border of the normal epidural space 27 generally defined by the ligamentum flavum 26, which is shown in its normal, non-thickened state in FIG. 1.

Figure 2:
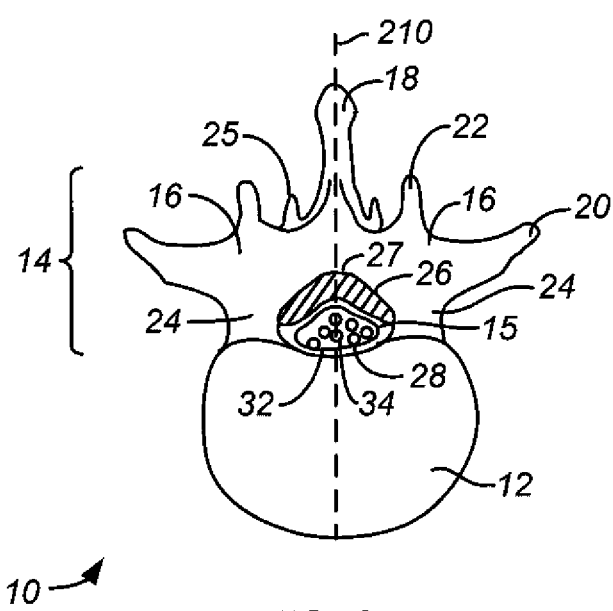
FIG. 2 is an illustration of the same section as FIG. 1, showing the spinal canal with the dural sac and a thickened ligamentum flavum therein.

FIG. 2 illustrates a case of spinal stenosis resulting from a thickened ligamentum flavum 26. Since vertebral foramen 15 is defined and surrounded by the relatively rigid bone its volume is essentially constant. Thus, thickening of ligamentum flavum 26 within vertebral foramen 15 call eventually result in compression of spinal cord 28. In particular, the thickened ligamentum flavum 26 may exert a compressive force on the posterior surface of dural sac 32. In addition, thickening of ligamentum flavum 26 may compress the blood vessels and fat occupying epidural space 27.

Compression of spinal cord 28, particularly in the lumbar region, may result in low back pain as well as pain or abnormal sensations in the legs. Further, compression of the blood vessels in the epidural space 27 that houses the nerves of the cauda equina may result in ischemic pain termed spinal claudication.

In order to relieve the symptoms associated with a thickened or enlarged ligamentum flavum 26, methods, techniques, and devices described herein may be employed to reduce the compressive forces exerted by the thickened ligamentum flavum on spinal cord 28 and the blood vessels in epidural space 27 (e.g., decompress spinal cord 28 and blood vessels in epidural space 27). In particular, compressive forces exerted by the thickened/enlarged ligamentum flavum 26 may be reduced by embodiments of a minimally invasive ligament decompression procedure described herein. In some embodiments, the minimally invasive ligament decompression procedure may be performed percutaneously to reduce the size of ligamentum flavum 26 by excising portions of ligamentum flavum 26. In particular, in some embodiments of the minimally invasive ligament decompression procedure, the ligamentum flavum 26 is accessed, cut and removed ipsilaterally (i.e., on the same side of vertebral arch 14) by a percutaneous cranial-caudal approach. Such an embodiment of the minimally invasive ligament decompression procedure may be described hereinafter as Ipsilateral Approach minimally invasive ligament decompression Procedure.

Creation of a Safety Zone

As shown in FIGS. 1 and 2, ligamentum flavum 26 is posteriorly apposed to spinal cord 28. Thus, placement of tools within ligamentum flavum 26 to excise portions of ligamentum flavum 26 creates a risk of for inadvertent damage to the spinal cord 28, dural sac 32, and/or nerves 34. Thus, in preferred embodiments of the procedures described herein, prior to insertion of tissue removal tools into the ligamentum flavum 26, a gap is advantageously created between ligamentum flavum 26 and spinal cord 28 to provide a safety zone between ligamentum flavum 26 and spinal cord 28.

Figure 3:
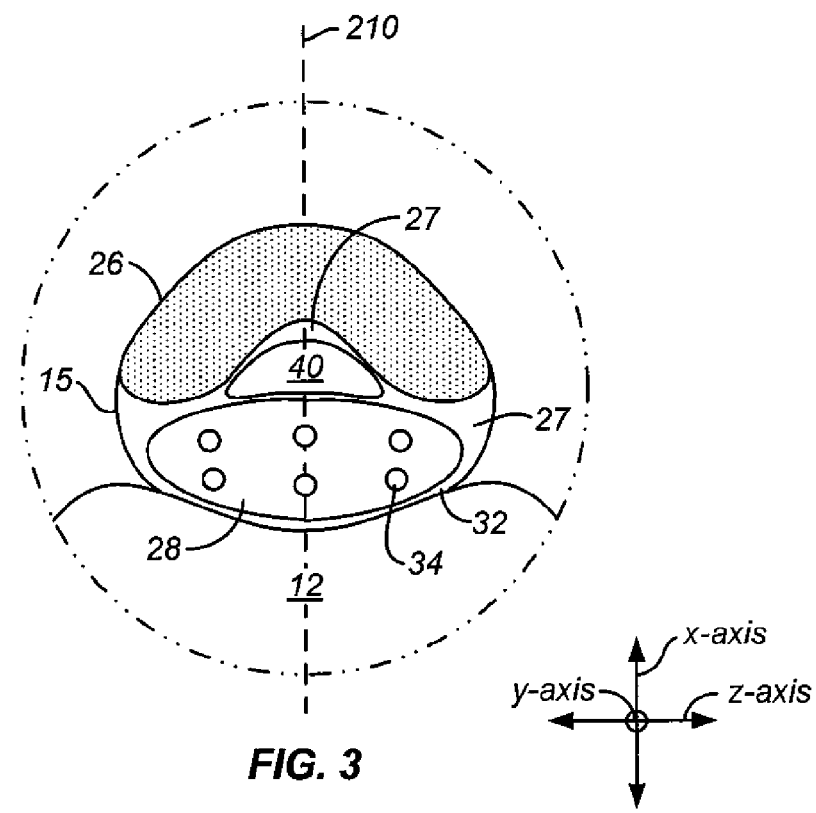
FIG. 3 is an enlarged cross-section of a vertebral foramen, showing a safety zone created by compression of the dural sac.

FIG. 3 illustrates an enlarged cross-sectional view of a vertebral foramen 15 within a vertebra. Vertebral foramen 15 includes epidural space 27 and spinal cord 28 containing nerves 34 and CSF within dural sac 32 Further, a thickened/enlarged ligamentum flavum 26 extends into vertebral foramen 15. To reduce the risk of damage to dural sac 32 and spinal cord 28, a safety zone 40 is created between ligamentum flavum 26 and dural sac 32.

As previously described, spinal cord 28 comprises nerves 34 surrounded by CSF and is contained within dural sac 32. Since more than 90% of the volume of dural sac 32 in the lumbar, region is filled by CSF, dural sac 32 is highly compressible. Thus, even when stenosis is causing compression of spinal cord 28, in most cases it is possible to temporarily compress spinal cord 28 further. Thus, according to preferred embodiments, dural sac 32 is further compressed in the region of interest by injecting a fluid into epidural space 27 to create safety zone 40. The presence of the injected fluid comprising safety zone 40 gently applies an additional compressive force to the outer surface of dural sac 32 so that at least a portion of the CSF within dural sac 32 is forced out of dural sac 32 in the region of interest, resulting in safety zone 40 between dural sac 32 and ligamentum flavum 26.

According to some embodiments, dural sac 32 is compressed by injecting a standard radio-opaque non-ionic myelographic contrast medium or other imagable or non-imagable medium into epidural space 27 in the region of interest. This is preferably accomplished with a percutaneous injection. Sufficient injectable fluid is preferably injected to displace the CSF out of the region of interest and compress dural sac 32 to at least a desired degree. The injected medium is preferably substantially contained within the confines of epidural space 27 extending to the margins of the dural sac 32. The epidural space is substantially watertight and the fatty tissues and vascularization in epidural space 27, combined with the viscous properties of the preferred fluids, serve to substantially maintain the injected medium in the desired region of interest. This novel method for protecting spinal cord 28 column may be referred to hereinafter as "contrast-guided dural protection."

Figure 4:
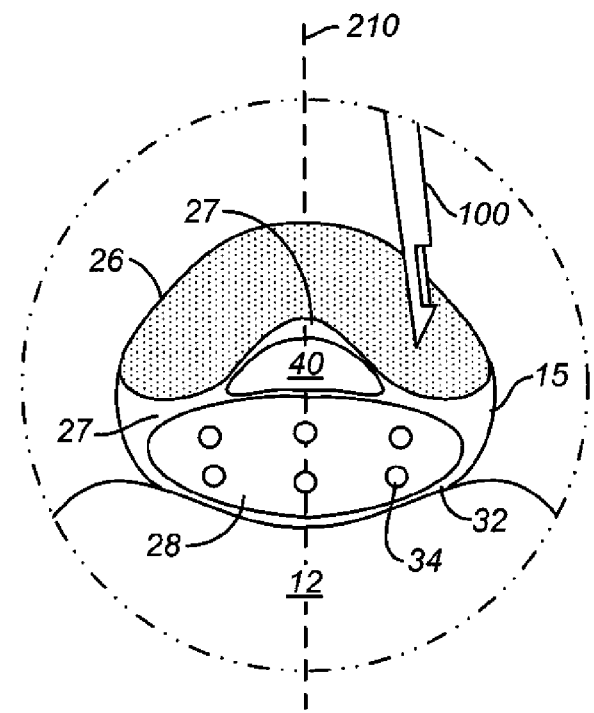
FIG. 4 is the cross-section of FIG. 3, showing a tissue excision tool positioned in the ligamentum flavum according to a first method (ILAMP)
Figure 5:
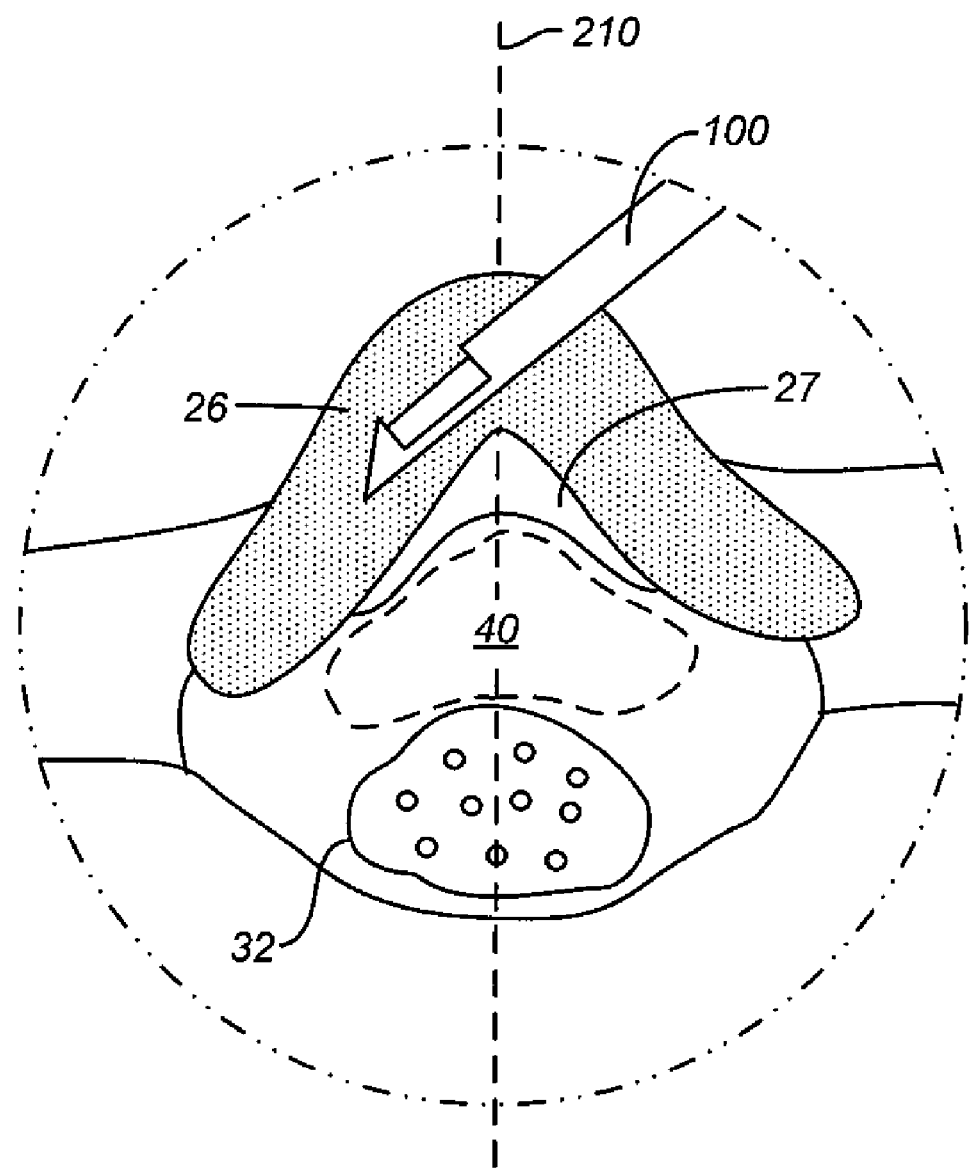
FIG. 5 is the cross-section of FIG. 3, showing a tissue excision tool positioned in the ligamentum flavum according to an alternative method (MILD)

Once a safety zone 40 has been created, a tool 100 may be inserted into the ligamentum flavum 26, as will be described in more detail below. Tool 100 may comprise any suitable device, tool or instrument for relieving stenosis caused by the thickened/enlarged ligamentum flavum 26 including without limitation, embodiments of tissue excision devices and tissue retraction devices described in more detail below. Further, as best illustrated in FIG. 4, tool 100 is inserted and positioned in the ligamentum flavum 26 on the same side (ipsilateral) of median plane 210 as tool 100 percutaneously accesses the body, such that tool 100 does not cross median plane 210. In another embodiment, as best illustrated in FIG. 5, tool 100 is positioned in the ligamentum flavum 26 on the opposite side of median plane 210 as tool 100 percutaneously accesses the body, such that tool 100 crosses median plane 210.

While it is preferred that the tip of tool 100 remain within ligamentum flavum 26 as shown, the presence of safety zone 40 reduces the likelihood that dural sac 32 will be damaged, even if the tool breaks through the anterior surface of ligamentum flavum 26.

Because the present techniques are preferably performed percutaneously, certain aspects of the present invention may be facilitated by imaging. Imaging windows (e.g., a fluoroscopic window of access—FWA) may be employed to aid in performance of all or, part of the procedures described herein. For instance, an imaging window may be employed to aid in insertion of tool 100 into ligamentum flavum 26 as shown in FIG. 4A Preferable imaging windows/views are described in mote detail below.

In this context, the spine can be imaged using any suitable technology, including without limitation, 2D fluoroscopy, 3D fluoroscopy, CT, MRI, ultrasound or with direct visualization with fiber optic or microsurgical techniques. Stereotactic or computerized image fusion techniques are also suitable. Fluoroscopy is currently particularly well-suited to the techniques disclosed herein. Flouroscopic equipment is safe and easy to use, readily available in most medical facilities, relatively inexpensive. In a typical procedure, using direct biplane fluoroscopic guidance and local anesthesia, epidural space 27 is accessed for injection of contrast media adjacent to the surgical site.

If the injected medium is radio-opaque, as are for example myelographic contrast media, the margins of expanded epidural space 27 will be readily visible using fluoroscopy or CT imaging. Thus, safety zone 40 created by the present contrast-guided dural compression techniques can reduce the risk of damage to dural sac 32 and spinal cord 28 during minimally invasive ligament decompression procedures to remove or displace portions of ligamentum flavum 26 and/or laminae 16 in order to treat spinal stenosis.

Injectable Medium

If desired, the injected medium can be provided as a re-absorbable water-soluble gel, so as to better localize safety zone 40 at the site of surgery and reduce leakage of this protective layer from the vertebral/spinal canal. An injectable gel is a significant improvement on prior epidural injection techniques. The gel is preferably substantially more viscid than conventional contrast media and the relatively viscid and/or viscous gel preferably tends to remain localized at the desired site of treatment as it does not spread as much as standard liquid contrast media that are used in epidurography. This may result in more uniform compression of dural sac 32 and less leakage of contrast out of the vertebral/spinal canal. In addition, preferred embodiments of the gel are re-absorbed more slowly than conventional contrast media, allowing for better visualization during the course of the surgical procedure.

In some embodiments, a contrast agent can be included in the gel itself, so that the entire gel mass is imagable. In other embodiments, an amount of contrast can be injected first, followed by the desired amount of gel, or an amount of gel can be injected first, followed by the desired amount of contrast. In this case, the contrast agent is captured on the surface of the expanding gel mass, so that the periphery of the mass is imagable.

Any standard hydrophilic-lipophilic block copolymer (Pluronic) gel such as are known in the art would be suitable and other gels may be used as the injectable medium. The gel preferably has an inert base. In certain embodiments, the gel material is liquid at ambient temperatures and can be injected through a small bore, such as a 27 gauge needle. The gel then preferably becomes viscous when warmed to body temperature after being injected. The viscosity of the gel can be adjusted through the specifics of the preparation. The gel or other fluid is preferably sufficiently viscid or viscous at body temperature to compress and protect dural sac 32 in the manner described above and to remain sufficiently present in the region of interest for at least about 30 minutes. Thus, in some embodiments, the injected gel attains a viscosity that is two, three, six or even ten times that of the fluids that are typically used for epidurograms.

In certain embodiments, the injected medium undergoes a reversible change in viscosity when warmed to body temperature so that it can be injected as a low-viscosity fluid, thicken upon injection into the patient, and be returned to its low-viscosity state by cooling. In these embodiments, the injected medium is injected as desired and thickens upon warming, but can be removed by contacting it with a heat removal device, such as an aspirator that has been provided with a cooled tip. As a result of localized cooling, the gel reverts to its initial non viscous liquid state and can be easily suctioned up the cooled needle or catheter.

An example of a suitable contrast medium having the desired properties is Omnipaque® 240 available from Nycomed, N.Y., which is a commercially available non-ionic iodinated myelographic contrast medium. Other suitable injectable media will be known to those skilled in the art. Because of the proximity to spinal cord 28 and spinal nerves 34, it is preferred not to use ionic media in the injectable medium The preferred compositions are reabsorbed relatively rapidly after the procedure. Thus any residual gel compression on dural sac 32 after the minimally invasive ligament decompression procedure dissipates relatively quickly. For example, in preferred embodiments, the gel would have sufficient viscosity to compress dural sac 32 for thirty minutes, and sufficient degradability to be substantially reabsorbed within approximately two hours.

The injected contrast medium further may further include one or more bioactive agents. For example, medications such as those used in epidural steroid injection (e.g. Depo medrol, Celestone Soluspan) may be added to the epidural gel to speed healing and reduce inflammation, scarring and adhesions. The gel preferably releases the steroid medication slowly and prolongs the anti-inflammatory effect, which can be extremely advantageous. Local anesthetic agents may also be added to the gel. This prolongs the duration of action of local anesthetic agents in the epidural space to prolong pain relief during epidural anesthesia. In this embodiment the gel may be formulated to slow the reabsorption of the gel.

The present gels may also be used for epidural steroid injection and perineural blocks for management of acute and chronic spinal pain. Thrombin or other haemostatic agents can be added if desired, so as to reduce the risk of bleeding.

In some embodiments, the gel may also be used as a substitute for a blood patch if a CSF leak occurs. The gel may also be used as an alternative method to treat lumbar puncture complications such as post-lumbar puncture CSF leak or other causes of intracranial hypotension. Similarly, the gel may be used to patch postoperative CSF leaks or dural tears. If the dural sac were inadvertently torn or cut, then gel could immediately serve to seal the site and prevent leakage of the cerebral spinal fluid.

Ipsilateral Approach for Minimally Invasive Ligament Decompression Procedure

Once safety zone 40 has been created, the margins of epidural space 27 are clearly demarcated by the injected medium and may be visualized radiographically if an imageable medium has been used. As mentioned above, percutaneous procedures can then more safely be performed on ligamentum flavum 26 and/or surrounding tissues with reduced potential for injuring dural sac 32 and spinal cord 28.

A variety of suitable techniques may be employed to reduce the size of the thickened/enlarged ligamentum flavum 26, thereby decompressing spinal cord 28 as well as blood vessels contained within the epidural space 27. Examples of suitable decompression techniques include without limitation, removal of tissue from ligamentum flavum 26, laminectomy, laminotomy, and retraction and anchoring of ligamentum flavum 26. In some embodiments, all or a portion of ligamentum flavum 26 is excised using a tissue excision tool (e.g., tool 100). Embodiments of tissue excision tools are described in more detail below.

Accessing ligamentum flavum 26 with a tool 100 to remove portions of ligamentum flavum 26 can present significant challenges For instance, in some conventional approaches to correct stenosis caused by an enlarged ligamentum flavum, an incision is made in the back of the patient and then the muscles and supporting structures of the vertebral column (spine) are stripped away, exposing the posterior aspect of the vertebral column. Subsequently, the thickened ligamentum flavum is exposed by removal of a portion of vertebral arch 14, often at lamina 16, which encloses the anterior portion of the spinal canal (laminectomy). The thickened ligamentum flavum ligament can then be excised by sharp dissection with a scalpel or punching instruments. However, this approach is usually performed under general anesthesia and typically requires an extended hospital stay, lengthy recovery time and significant rehabilitation. Referring briefly to FIG. 2, as another example, some minimally invasive ligament decompression procedures access ligamentum flavum 26 percutaneously by boring a hole through the vertebral arch 14 of vertebra 10, often through a lamina 16. A cannula and/or tool 100 may be passed through the bore and/or anchored to the bore to access ligamentum flavum 26 for excisions However, while such a minimally invasive ligament decompression approach is minimally invasive and reduces recovery time, such an approach requires the additional step of boring a hole in the posterior of the vertebra 10 of interest. Thus, in some cases it will be preferable to employ a minimally invasive ligament decompression that percutaneously accesses ligamentum flavum 26 without the need to cut or bore through the vertebrae.

Figure 6:
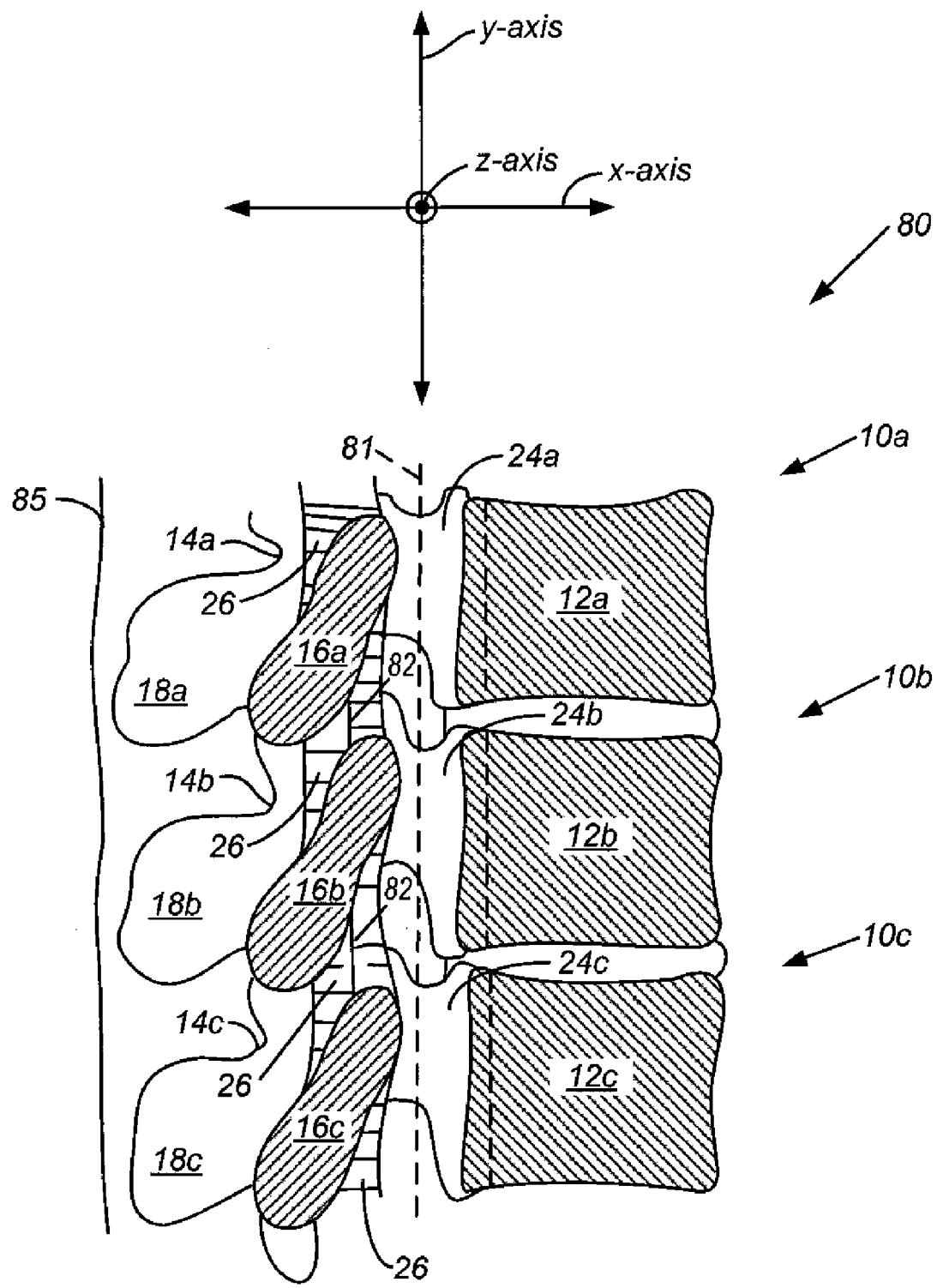
FIG. 6 is a partial cross-section of the lumbar portion of the vertebral column taken along lines 6-6 in FIG. 1.

FIG. 6 is a partial cross-sectional lateral view of a segment of a vertebral column 80. The segment of vertebral column 80 illustrated in FIG. 6 includes three vertebrae 10*a*, 10*b*, and 10*c*. Each vertebra 10*a*, 10*b*, 10*c* includes a vertebral body 12*a*, 12*b*, 12*c*, that supports a vertebral arch 14*a*, 14*b*, 14*c*, respectively. Vertical body 12*a*, 12*b*, 12*c* is anterior to vertebral arch 14*a*, 14*b*, 14*c*, respectively. Each vertebral arch 14*a*, 14*b*, 14*c* together with vertebral body 12*a*, 12*b*, 12*c*, respectively, encloses a vertebral foramen 15*a*, 15*b*, 15*c*. The succession of vertebral foramen 15*a*, 15*b*, 15*c* in adjacent vertebrae 10*a*, 10*b*, 10*c* define vertebral canal 81 (spinal canal) that runs along the length of vertebral column 80. Vertebral canal 81 contains the spinal cord (not shown in FIG. 6).

As previously described, each vertebral arch 14*a*, 14*b*, 14*c* includes two pedicles 24*a*, 24*b*, 24*c*, which project posteriorly to meet two lamina 16*a*, 16*b*, 16*c*, respectively It is to be understood that in this view, one pedicle has been removed from each vertebra 10*a*, 10*b*, 10*c* and only the cross-section of one lamina 16*a*, 16*b*, 16*c* is visible. The two lamina 16*a*, 16*b*, 16*c* meet posteriomedially to form the spinous process 18*a*, 18*b*, 18*c*, respectively.

Lamina 16*a*, 16*b*, 16*c* of adjacent vertebra 10*a*, 10*b*, 10*c* are connected by ligamentum flavum 26 (shown in cross-section). The relatively elastic ligamentum flavum 26 extends almost vertically from superior lamina to inferior lamina of adjacent vertebrae. In particular, ligamentum flavum 26 originates on the inferior surface of the laminae of the superior vertebrae and connects to the superior surface of the laminae of the inferior vertebrae. For instance, ligamentum flavum 26 originates on the inferior surface of lamina 16*a* of superior vertebra 10*a* and connects to the superior surface of lamina 16*b* of the inferior vertebra 10*b*. Thus, ligamentum flavum 26 spans an interlaminar space 82 (i.e., space between laminae of adjacent vertebrae). Interlaminar space 82 is generally the space between laminae of adjacent vertebrae in spinal column 80.

Still referring to FIG. 6, each lamina 16*a*, 16*b*, 16*c* comprises a relatively broad flat plate of bone that extends posteromedially and slightly inferiorly from pedicles 24*a*, 24*b*, 24*c*, respectively. Along the length of vertebral column 80, the lamina 16*a*, 16*b*, 16*c* overlap like roofing shingles, with each lamina substantially parallel to and at least partially overlapping the adjacent inferior lamina. Further, the adjacent substantially parallel laminae are separated by the intervening ligamentum flavum 26 and interlaminar space 82. For instance, lamina 16*a* is substantially parallel to and partially overlaps adjacent inferior lamina 16*b* and is separated from lamina 16*b* by ligamentum flavum 26 and interlaminar space 82.

Figure 7:
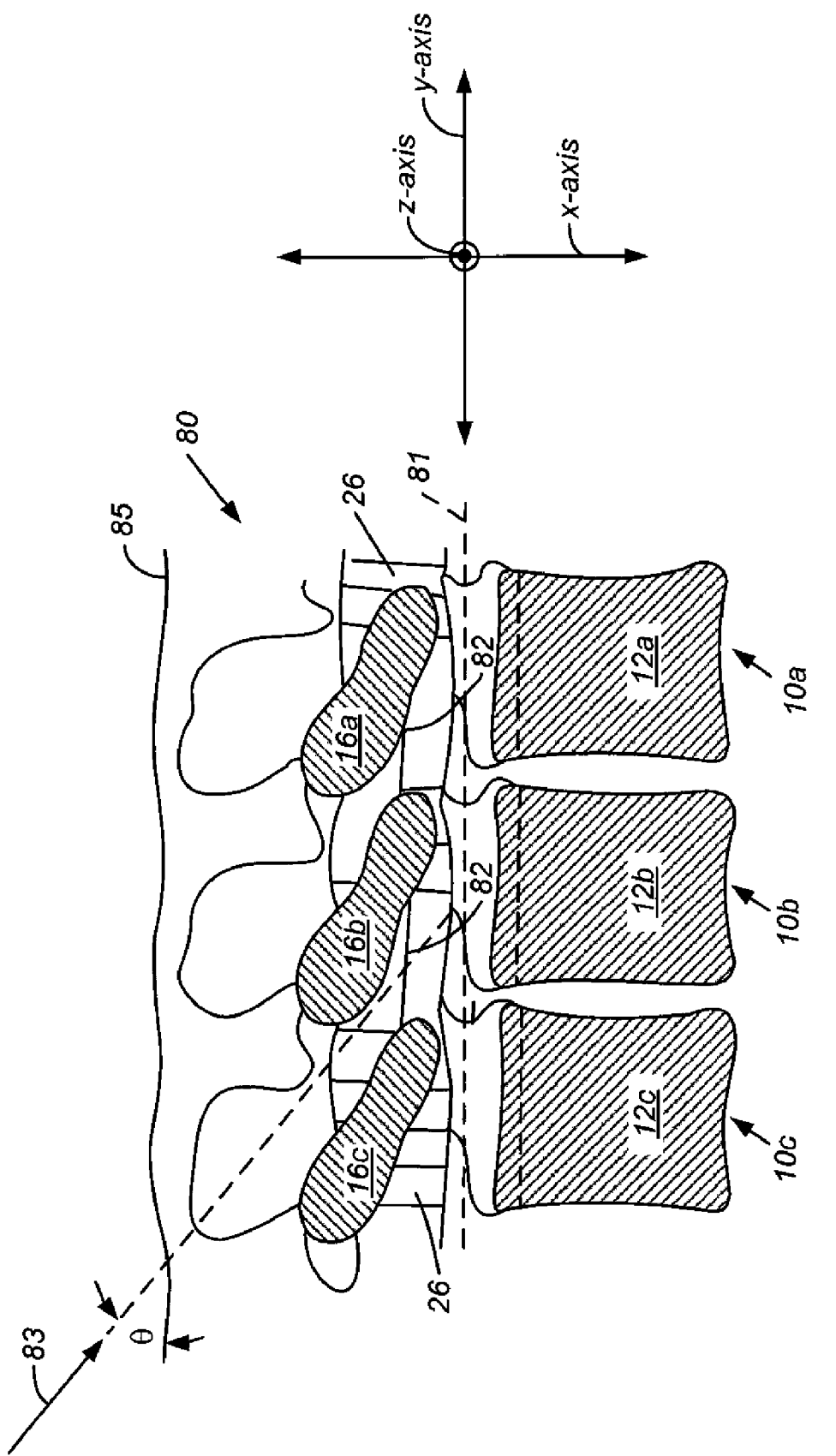
FIG. 7 is the cross-section of FIG. 6, showing the orientation of an imaging tool relative to the vertebral column.

FIG. 7 illustrates vertebral column 80 as it may be oriented with the anterior side positioned down and posterior back surface 85 positioned upward, as may be encountered during a spinal procedure or surgery. In addition, in the embodiment illustrated in FIG. 6, ligamentum flavum 26 is thickened/enlarged, resulting in spinal stenosis. In particular, the anterior portions of enlarged ligamentum flavum 26 are extending into spinal canal 81, potentially exerting compressive forces on the spinal cord (not shown) that resides within spinal canal 81.

As previously discussed, to relieve compressive forces on the spinal cord and hence relieve the associated symptoms of spinal stenosis, portions of ligamentum flavum 26 may be excised. However, to percutaneously excise portions of ligamentum flavum 26 via minimally invasive techniques, the innate structure of vertebral column 80 and each vertebra may present significant imaging challenges. For instance, lateral imaging windows/views of ligamentum flavum 26 substantially in the direction of the z-axis may be obscured by the various processes of the vertebrae (e.g., transverse processes, superior articular processes, inferior articular processes), the laminae of each vertebra, etc. Further, some anterior-posterior (A-P) imaging windows/views of ligamentum flavum 26 substantially in the direction of the x-axis may also be obscured by the laminae. In particular, in the A-P radiographic imaging planes substantially in the direction of the x-axis, the posterior edges of parallel laminae overlap and obscure ligamentum flavum 26 and interlaminar space 82, particularly the anterior portions of ligamentum flavum 26 and interlaminar space 82 closest to spinal canal 81. However, with an imaging window/view in a plane substantially parallel to the X-Y plane, at an angle .theta. generally in the direction of arrow 83, and slightly lateral to the spinous process, interlaminar space 82 and ligamentum flavum 26 may be viewed without significant obstruction from neighboring laminae. In other words, imaging windows/views generally aligned with arrow 83 (FIG. 7) allow a more direct view of interlaminar space 82 and ligamentum flavum 26 from the posterior back surface with minimal obstruction by the vertebrae, laminae in particular.

Typically, the long axis of the substantially parallel laminae (e.g., laminae 16*a*, 16,*b*, 16*c*) and interlaminar spaces (e.g, interlaminar spaces 82) are generally oriented between 60 and 75 degrees relative to posterior back surface 85. Thus, preferably the imaging means (e.g., x-ray beam, fluoroscopy tube, etc.) is positioned generally in the direction represented by arrow 83, where $\theta$ is substantially between 60 and 75 degrees relative to the anterior back surface 85. In other words, the imaging means is positioned substantially parallel to the surface of the laminae. The resulting imaging window/view, termed "caudal-cranial posterior view" hereinafter, permits a clearer, more direct, less obstructed view of interlaminar space 82 and ligamentum flavum 26 from the general posterior back surface 85. The caudal-cranial posterior view permits a relatively clear view of interlaminar space 82 and ligamentum flavum 26 in directions generally along the y-axis and z-axis. However, the caudal-cranial posterior view by itself may not provide a clear imaging window/view of interlaminar space 82 and ligamentum flavum 26 in directions generally along the x-axis In other words, the caudal-cranial posterior view by itself may not provide a clear imaging window/view that can be used to accurately determine the posterior-anterior depth, measured generally along the x-axis, of a device across the ligamentum flavum 26.

Thus, in preferred embodiments, an additional imaging window/view, termed "caudal-cranial posterior-lateral view" hereinafter, is employed to provide a clearer, unobstructed view of interlaminar space 82 and ligamentum flavum 26 in directions generally along the y-axis and z-axis. The caudal-cranial posterior-lateral view is generated by orienting an imaging means generally at an angle $\theta$ relative to outer surface of the patient and also angling such imaging means laterally in an oblique orientation, revealing a partial lateral view of interlaminar space 82 occupied by ligamentum flavum 26 on the anterior side of the lamina and posterior to the underlying dural sac (not shown) and spinal cord (not shown).

By employing at least one of the caudal-cranial posterior view and the caudal-cranial posterior-lateral views, relatively clear imaging windows/views of the interlaminar space 82 and ligamentum flavum 26 in directions along the x-, y-, and z-axis may be achieved.

Figure 8:
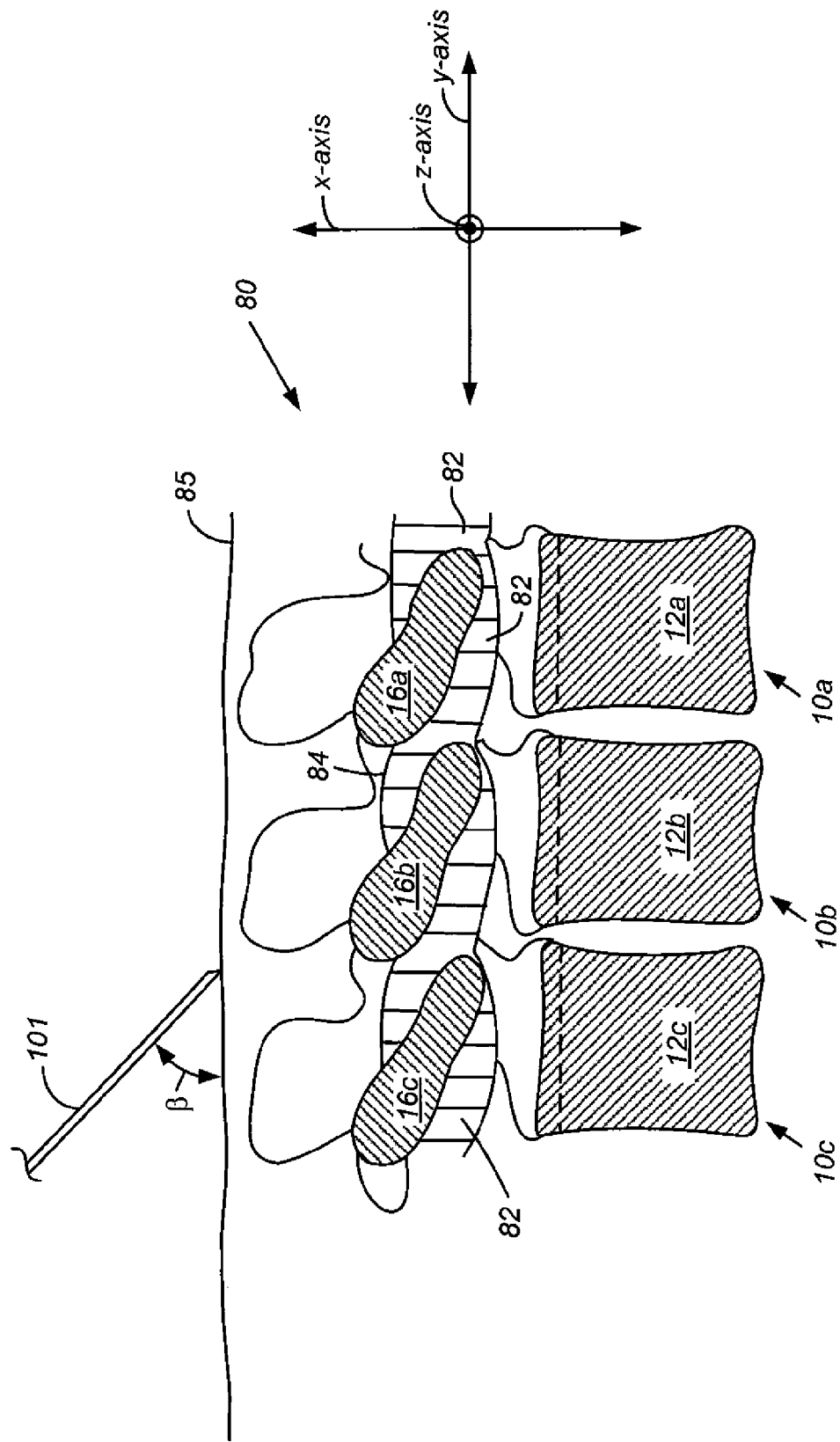
FIG. 8 is the cross-section of FIG. 6, showing the orientation of an instrument relative to the vertebral column.

FIG. 8 illustrates vertebral column 80 and an instrument 101. Once unobstructed imaging windows/views of interlaminar space 82 and ligamentum flavum 26 are established in the manner described above, instrument 101 is employed to percutaneously access interlaminar space 82 and ligamentum flavum 26. Instrument 101 may be any suitable device necessary to perform the minimally invasive ligament decompression procedures described herein including without limitation, a cannula, a tissue excision tool, or combinations thereof. Tissue excision tools are described in more detail below.

More specifically, using images of the interlaminar space 82 and ligamentum flavum 26 obtained from the desired direction(s), (e.g., caudal-cranial posterior view and the caudal-cranial posterior-lateral view), instrument 101 can be employed to penetrate the skin and soft tissue in the posterior back surface 85 of the patient. In preferred embodiments, the skin entry point for instrument 101 is between 5 and 10 cm inferior (caudal to) the posterior surface of the interlaminar space 82 of interest. For instance, if the portion of ligamentum flavum 26 between lamina 16*a* and lamina 16*b* is the area of interest, then instrument 101 may be inserted into the patient's back about 5 to 10 cm inferior to posterior surface 84 of interlaminar space 82.

Referring now to FIG. 8, instrument 101 is preferably initially inserted into the posterior tissue and musculature of the patient generally parallel to the longitudinal axis of spinal column 80. In other words, the angle .beta. between the posterior back surface 85 and tool 100 is between 0 and 10 degrees when tool 100 is initially inserted. Further, instrument 101 is preferably inserted into the posterior tissue and musculature of the patient on the same side (ipsilateral) of the median plane as the area of interest (e.g., the targeted portion of ligamentum flavum 26), as best seen in FIG. 4. Once tool 100 is inserted into the posterior tissue and musculature of the patient, instrument 101 then may be oriented 5 to 90 degrees relative to the posterior back surface 85 in order to create a trajectory across ligamentum flavum 26 in the area of interest. It is to be understood that once instrument 101 is inserted into the patient's posterior back surface 85, the ends of instrument 101 are free to pivot about the insertion location in posterior back surface 85 in the general direction of the y-axis and the z-axis, and may be advanced posteriorly or anteriorly generally in the direction of the x-axis.

Once inserted into the posterior tissue and musculature of the patient, instrument 101 can be positioned to provide a pathway across interlaminar space 82 in the area of interest, generally towards the anterior surface of the lamina superior to the area of interest. For example, if interlaminar space 82 between lamina 16*a* and lamina 16*b* is the area of interest, instrument 101 is positioned to provide a trajectory that will allow a cutting instrument to be inserted across interlaminar space 82 between lamina 16*a* and lamina 16*b* towards the anterior surface of lamina 16*a* (superior lamina).

By switching between the caudal-cranial posterior view and the caudal-cranial posterior-lateral view, or by viewing both the caudal-cranial posterior view and the caudal-cranial posterior-lateral view at the same time, instrument 101, or an excision tool passing through instrument 101 (e.g., tool 100), can be advanced and inserted into ligamentum flavum 26 in the area of interest with more certainty than has heretofore been present. Once instrument 101, or an excision tool passing therethrough, is inserted into ligamentum flavum 26, portions of ligamentum flavum 26 may be excised so as to relieve pressure on the spinal nerves In some embodiments, resection can be performed generally from posterior to anterior across interlaminar space 82 and then laterally along the anterior portion of ligamentum flavum 26 if desired. The actual depth of the instrument tip in the general direction of the x-axis may be adjusted with guidance from the caudal-cranial posterior-lateral view and appropriate retraction/advancement of instrument 101 and appropriate adjustment of instrument 101 between 5 and 90 degrees relative to the posterior back surface 85.

In the manner described, portions of the ligamentum flavum can be excised by a percutaneous minimally invasive ligament decompression procedure. In particular, with the approach described and as best illustrated in FIGS. 4 and 6, ligamentum flavum 26 can be accessed, and portions thereof removed via the interlaminar space on the same lateral side (ipsilateral) of median plane 210 as the entry point for the cannula (e.g., instrument 101) and cutting instrument (e.g., tool 100). This approach may sometimes hereinafter be referred to as an ipsilateral approach to the minimally invasive ligament decompression Procedure.

Percutaneous Tissue Excision

Referring to FIG. 4, an excision tool 100 is shown schematically within ligamentum flavum 26. In particular, tool 100 has accessed ligamentum flavum 26 according to the ipsilateral approach to the minimally invasive ligament decompression procedure method previously described. Thus, tool 100 is positioned to excise portions of ligamentum flavum 26 on the same lateral side of median plane 210 as tool 100 is inserted. In other words, in the view shown in FIG. 4, tool 100 is inserted into the body on the right side of median plane 210 and enters ligamentum flavum 26 on the right side of median plane 210 to excise portions of ligamentum flavum 26 on the tight side of median plane 210. In FIG. 4, tool 100 does not cross median plane 210. FIG. 5 illustrates an embodiment of an alternative minimally invasive ligament decompression method in which tool 100 is positioned to excise portions of ligamentum flavum 26 on the opposite lateral side of median plane 210 as tool 100 is inserted. More specifically, tool 100 is inserted into the body on the rights side of median plane 210 and enters ligamentum flavum 26 on the right side of median plane 210, to excise portions of ligamentum flavum 26 on the left side of median plane 210. In FIG. 5, tool 100 crosses median plane 210.

Embodiments of the present tissue excision devices and techniques can take several forms. In the discussion below, the distal ends of the tools are described in detail. The construction of the proximal ends of the tools, and the means by which the various components disclosed herein are assembled and actuated, will be known and understood by those skilled in the art.

By way of example, in the embodiment illustrated in FIG. 9, device 100 may be a coaxial excision system 50 with a sharpened or blunt tip that is placed obliquely into the thickened ligamentum flavum 26 posterior to safety zone 40 under fluoroscopic guidance. Excision system 50 is preferably manufactured from stainless steel, titanium or other suitable durable biocompatible material. As shown in FIGS. 9-13, an outer needle or cannula 51 has an opening or aperture 52 on one side that is closed during insertion by an inner occluding member 54. Aperture 52 is readily visible under imaging guidance. Once needle 51 is positioned in the ligamentum flavum or other tissue removal site, inner occluding member 54 is removed or retracted so that it no longer closes aperture 52 (FIG. 10). Aperture 52 is preferably oriented away from the epidural space so as to further protect the underlying structures from injury during the surgical procedure. If it was not already present in the tool, a tissue-engaging means 56 is inserted through outer needle 51 to aperture 52 so that it contacts adjacent tissue, e.g. the ligamentum flavum, via aperture 52.

Tissue-engaging means 56 may be a needle, hook, blade, tooth or the like, and preferably has at least one flexible barb or hook 58 attached to its shaft. The barb 58 or barbs may extend around approximately 120 degrees of the circumference of the shaft. Barbs 58 are preferably directed towards the proximal end of the tool. When needle 56 is retracted slightly, barbs 58 allow it to engage a segment of tissue. Depending on the configuration of barbs 58, the tissue sample engaged by needle 56 may be generally cylindrical or approximately hemispherical. Once needle 56 has engaged the desired tissue, inner occluding means 54, which is preferably provided with a sharpened distal edge, is advanced so that it cuts the engaged tissue section or sample loose from the surrounding tissue. Hence occluding means 54 also functions as a cutting means in this embodiment. In alternative embodiments, such as FIGS. 14-18 discussed below, a cylindrical outer cutting element 60 may extended over outer needle 51 and used in place of occluding member 54 to excise the tissue sample.

Referring still to FIGS. 9-13, once the tissue sample has been cut, tissue-engaging needle 56 can be pulled back through outer needle 51 so that the segment of tissue can be retrieved and removed from the barbs (FIG. 12). The process or engaging and resecting tissue may be repeated (FIG. 13) until the canal is adequately decompressed.

Referring briefly to FIGS. 14-18, in other embodiments, a tissue-engaging hook 64 can be used in place of needle 56 and an outer cutting member 60 can be used in place of inner occluding member 54. Hook 64 may comprise a length of wire that has been bent through at least about 270°, more preferably though 315°, and still more preferably through about 405°. Alternatively or in addition, hook 64 may comprise Nitinol™, or any other resilient metal that can withstand repeated elastic deflections In the embodiment illustrated, hook 64 includes at least one barb 58 at its distal end. In some embodiments, hook 64 is pre-configured in a curvilinear shape and is retained within tool 100 by outer cutting member 60. When cutting member 60 is retracted, the curved shape of hook 64 urges its outer end to extend outward through aperture 52. If desired, hook 64 can be advanced toward the distal end of tool 100, causing it to extend farther into the surrounding tissue In some embodiments, hook 64 is provided with a camming surface 66. Camming surface 66 bears on the edge of opening 52 as hook 64 is advance or retracted and thereby facilitates retraction and retention of hook 64 as it is retracted into the tool. In these embodiments, hook 64 may not extend through aperture 52 until it has been advanced sufficiently for camming surface 66 to clear the edge of the opening. Hook 64 may alternatively be used in conjunction with an inner occluding member 54 in the manner described above. As above, hook 64 can be used to retrieve the engaged tissue from the distal end of the tool.

In still other embodiments, the tissue-engaging means may comprise a hook or tooth or the like that engages tissue via aperture 52 by being rotated about the tool axis. In such embodiments (not shown) and by way of example only, the tissue-engaging means could comprise a partial cylinder that is received in outer cannula 51 and has a serrated side edge. Such a device can be rotated via a connection with the tool handle or other proximal device. As the serrated edge traverses aperture 52 tissue protruding into the tool via the aperture is engaged by the edge, whereupon it can be resected and retrieved in the maimer disclosed herein.

In preferred embodiments, the working tip of tool 100 remains within the ligamentum flavum and does not penetrate the safety zone 40. Nonetheless, safety zone 40 is provided so that even an inadvertent penetration of the tool into the epidural space will not result in damage to the dural sac. Regardless of the means by which the tissue is engaged and cut, it is preferably retrieved from the distal end of the tool so that additional tissue segments can be excised without requiring that the working tip of the tool be repositioned. A tissue-removal device such as that described below is preferably used to remove the tissue from the retrieval device between each excision.

Tissue Removal

Each piece of tissue may be removed from barbs 58 by pushing tissue-engaging means 56 through an opening that is large enough to allow passage of the flexible barbs and supporting needle but smaller than the diameter of the excised tissue mass. This pushes the tissue up onto the shaft, where it can be removed with a slicing blade or the like or by sliding the tissue over the proximal end of the needle. Alternatively, needle 56 can be removed and re-inserted into the tool for external, manual tissue removal.

It is expected that in some embodiments, approximately 8-10 cores or segments of tissue will be excised and pushed up the shaft towards the hub during the course of the procedure. Alternatively, a small blade can be used to split the tissue segment and thereby ease removal of the segment from the device. If desired, a blade for this purpose can be placed on the shaft of needle 56 proximal to the barbs.

In an exemplary embodiment, shown in FIGS. 19-22, the tissue removal device may include a scraper 120 that includes a keyhole slot having a wide end 122 and a narrow end 124. To remove a tissue sample from needle 56 or hook 64, the tissue-engaging device with a mass of excised tissue 110 thereon can be retracted (pulled toward the proximal end of the tool) through wide end 122 of the slot and then re-inserted (pushed toward the distal end of the tool) through narrow end 124 of the slot. Narrow end 124 is large enough to allow passage of the barbed needle, but small enough to remove the tissue mass as the needle passes through. The removed tissue can exit the tool through an opening 113 in the tool body. By shuttling the tissue-engaging device through scraper 120 in this manner, each excised segment of tissue 110 can be removed from the device, readying the device for another excision.

Figure 23:
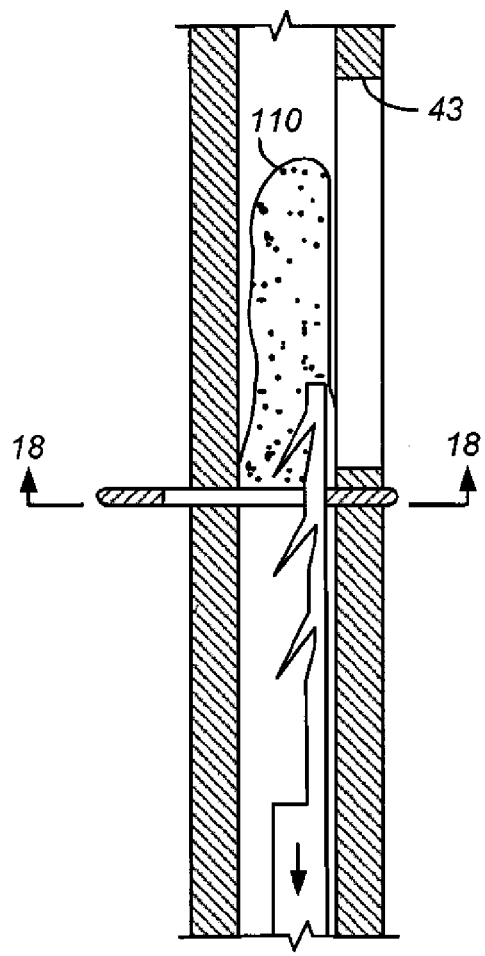
FIG. 23 is cross-section of a tissue-removal device constructed in accordance with an alternative embodiment of the invention.

In an alternative embodiment shown in FIG. 23, the tissue removal device may be constructed such that tissue is removed from the tissue-engaging device by retracting the tissue-engaging device through narrow end 124 of the slot. As above, narrow end 124 is large enough to allow passage of the shaft of the tissue-engaging device, but small enough to remove the tissue mass as the needle passes through. If the tissue-engaging device is constructed of a tough material, the barbs or the like will cut through the tissue and/or deform and release the tissue. As above, the removed tissue can exit the tool through an opening 113 in the tool body. By shuttling the tissue-engaging device through scraper 120 in this maimer, each excised segment of tissue 110 can be removed from the device, readying the device for another excision.

Figure 24:
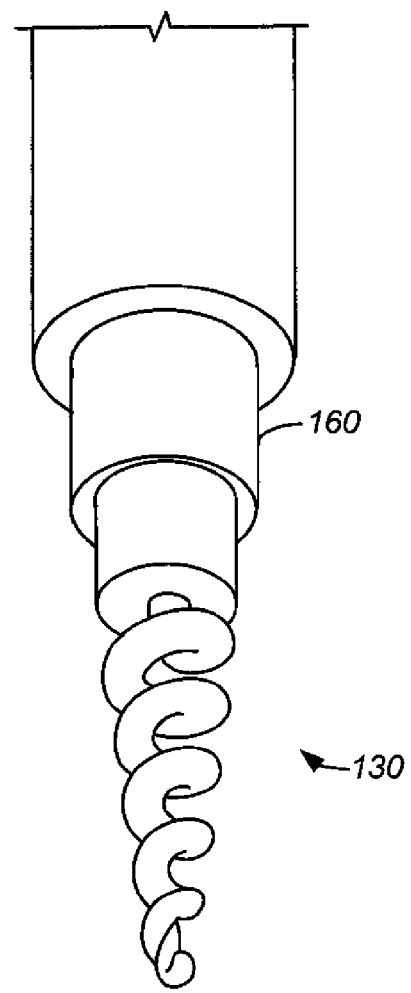
FIG. 24 shows an alternative embodiment of a grasping needle with a corkscrew shape.

In another alternative embodiment (not shown) an alternative mechanism for removing the tissue segment from needle 56 includes an adjustable aperture in a disc. After the tissue-bearing needle is pulled back through the aperture, the aperture is partially closed. Needle 56 and flexible hooks 58 then can pass through the partially closed aperture but the larger cylinder of tissue cannot. Thus the tissue segment is pushed back onto the shaft. The tissue segment can either be pulled off the proximal end of the shaft or cut off of it. A small blade may be placed just proximal to the barbs to help cut the tissue segment off the shaft. The variable aperture can formed by any suitable construction, including a pair of metal plates with matching edges that each define one half of a central opening. The two pieces may be held apart by springs. The aperture may be closed by pushing the two edges together. In other embodiments, this process can be mechanically automated by using a disc or plate with an opening that is adjustable by a variety of known techniques, including a slit screw assembly or flexible gaskets, Other cutting and/or grasping devices can be used in place of the system described above. For example, embodiments of the grasping mechanism include but are not limited to: needles with flexible barbs, needles with rigid barbs, corkscrew-shaped needles, and/or retaining wires. The corkscrew-shaped needle shown in FIG. 24 works by screwing into the ligamentum flavum in the manner that a corkscrew is inserted in a cork. After a screw 130 engages a segment of tissue, an outer cutting element 160 slides over the needle, cutting a segment of tissue in a manner similar to that of the previous embodiment. In some embodiments, the cutting element can be rotated as it cuts.

In other embodiments, shown in FIGS. 25-29, cannulated scalpel 71 houses a grasping device 70 that includes at least one pair of arcuate, closable arms 72. Closable arms 72 may be constructed in any suitable manner. One technique for creating closable arms is to provide a slotted sleeve 74, as shown. Slotted member 74 preferably comprises an elongate body 75 with at least one slot 76 that extends through its thickness but does not extend to either end of the body. Slot 76 is preferably parallel to the longitudinal axis of the sleeve. On either side of slot 76, a strip 77 is defined, with strips 77 being joined at each end of sleeve 74. It is preferred that the width of each strip 77 be relatively small. In some embodiments, it may be desirable to construct slotted member 74 from a portion of a hollow tube or from a rectangular piece that has been curved around a longitudinal axis. Be inner edge of each strip that lies along slot 76 forms an opposing edge 78. The width of the piece is the total of the width of strips 77 and slot 76.

Advancing one end of sleeve 74 toward the other end of sleeve 74 causes each strip 77 to buckle or bend. If strips 77 are prevented from buckling inward or if they are predisposed to bend in the desired direction, they will bend outward, thereby forming arcuate arms 72, which extend through aperture 52 of cannulated scalpel 71, as shown in FIG. 29. As they move away from the axis of body 75, arms 72 move apart in a direction normal to the axis of body 75. Likewise, moving the ends of sleeve 74 apart causes arms 72 to straighten and to move together and inward toward the axis of the device, as shown in FIG. 27. As the arms straighten, opposing edges 78 close and a segment of tissue can be captured between them. Tissue within the grasping device may then be resected or anchored via the other mechanisms described herein.

Closable arms 72 may include on their opposing edges 78 ridges, teeth, or other means to facilitate grasping of the tissue. In other embodiments, edges 78 may be sharpened, so as to excise a segment of tissue as they close. In these embodiments, closable arms 72 may also be used in conjunction with a hook, barbed needle, pincers or the like, which can in turn he used to retrieve the excised segment from the device.

Once aims 72 have closed on the tissue, if arms 72 have not cut the tissue themselves, the tissue can be excised using a blade such as cutting element 60 above. The excised tissue can be removed from the inside of needle 51 using a tissue-engaging hook 64 or other suitable means. The process of extending and closing arms 72, excising the tissue, and removing it from the device can be repeated until a desired amount of tissue has been removed.

If desired, this cycle can be repeated without repositioning the device in the tissue. Alternatively, the tool can be rotated or repositioned as desired between excisions It is possible to rotate or reposition the tool during an excision, but it is expected that this will not generally be preferred. Furthermore, it is expected that the steps of tissue excision and removal can be accomplished without breaching the surface of the ligament, i.e. without any part of the device entering the safety zone created by the injected fluid. Nonetheless, should the tool leave the working zone, the safety zone will reduce the risk of injury to the dural sac.

Ligament Retraction

In some embodiments, the spinal canal may also be enlarged by retracting the ligamentum flavum, either with or without concurrent resection. Retraction is preferably but not necessarily performed after dural compression has been used to provide a safety zone. In addition, the dural compression techniques described above have the effect of pressing the ligamentum flavum back out of the spinal canal and thereby making it easier to apply a restraining means thereto.

Figure 30:
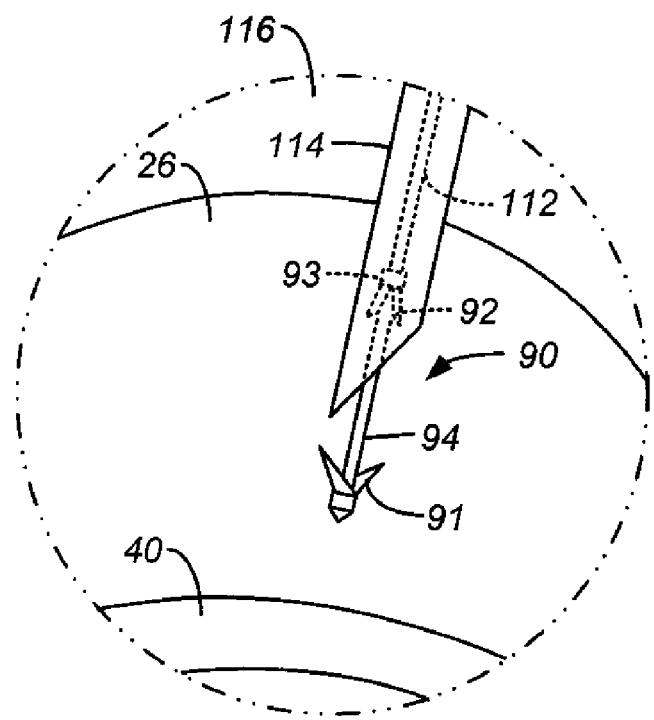
FIG. 30 is a schematic illustration of one embodiment of a double-ended ligament anchor being deployed in a ligamentum flavum.

Thus, in preferred embodiments, after a safety zone is created by epidural injection of contrast medium or gel, a retraction device 90 as shown in FIG. 30 is used to retract and compress the thickened soft tissues around the posterior aspect of the spinal canal, thereby increasing the available space for the dural sac and nerves In the embodiment shown, retraction device 90 is a double-headed anchor that includes at least one distal retractable tissue-engaging member 91 and at least one proximal tissue-engaging member 92, each of which are supported on a body 94 Retraction device 90 is preferably constructed from an implantable, non-biodegradable material, such as titanium or stainless steel, but may alternatively be polymeric or any other suitable material. In certain preferred embodiments, body 94 is somewhat flexible. In some instances, flexibility in body 94 may facilitate the desired engagement of barbs 91, 92. Barbs 91, 92 may comprise hooks, arms, teeth, clamps, or any other device capable of selectively engaging adjacent tissue. Barbs 91, 92 may have any configuration that allows them to engage the ligamentum flavum and/or surrounding tissue. Similarly, barbs 91, 92 may be covered, sheathed, pivotable, retractable, or otherwise able to be extended from a first position in which they do not engage adjacent tissue to a second position in which they can engage adjacent tissue.

FIG. 30 shows schematically the distal and proximal retractable arms 91, 92 of a preferred ligament anchor 90. The proximal end of the anchor preferably includes a threaded connector 93 or other releasable mechanism that attaches to a support shaft 112. Ligament anchor 90 may be attached to support shaft 112 and sheathed in a guide housing 114. The distal and proximal barbs 91, 92 are prevented by guide housing 114 from engaging surrounding tissue. Housing 102 is preferably a metal or durable plastic guide housing.

Figure 31:
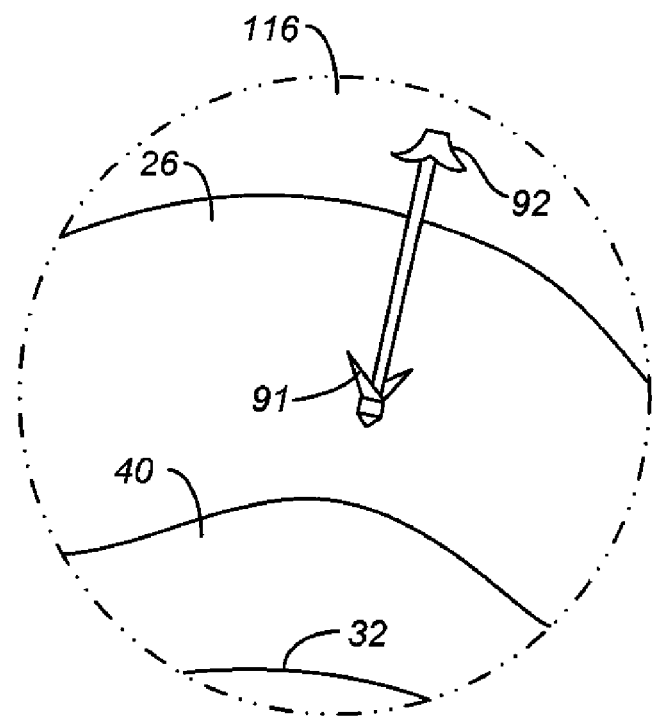
FIG. 31 shows the device of FIG. 30 after full deployment.

The distal end of the device is preferably positioned in the ligamentum flavum under fluoroscopic guidance. If desired, an accessway through the lamina may be provided using an anchored cannula or the like. The device is held in position by support shaft 112. Distal barbs 91 are unsheathed and optionally expanded by pulling back guide housing 114, as shown in FIG. 30. Distal barbs 91 are secured in the ligamentum flavum by pulling back on the support shaft 112. With barbs 91 engaging the tissue, the ligamentum flavum is retracted posteriorly by pulling back on support shaft 112. While maintaining traction on the now-retracted ligament, proximal barbs 92 are uncovered and expanded by retracting guide housing 114, as shown in FIG. 31. Barbs 92 are preferably positioned in the soft tissues 116 in the para-spinal region so that the device is firmly anchored behind the posterior elements of the spinal canal. Once the proximal end of the anchor is engaged, support shaft 112 may be detached from body 94 as shown in FIG. 31. In this manner, the posterior margin 95 of the ligamentum flavum can be held in a retracted position, thereby expanding the canal. The procedure can then be repeated on adjacent portions of the ligamentum flavum until it is sufficiently retracted.

In an alternative embodiment, the proximal end of ligament anchor 90 may be adapted to engage the lamina. This may be accomplished by having the arm posterior to the lamina or by using the laminotomy and suturing the device to the lamina there. A knotted or knotless system or a suture plate can be used.

A second embodiment of the present method uses a plurality of retraction devices 90. In this embodiment, the retraction device is inserted through one lamina in an oblique fashion, paralleling the opposite lamina. After the distal anchor is deployed, the retraction device is pulled back and across the ligamentum flavum, thereby decompressing the opposite lateral recess of the spinal canal. This is repeated on the opposite side. This same device can also be deployed with a direct approach to the lateral recess with a curved guide housing.

While retraction device 90 is describe above as a double-headed anchor, it will be understood that other devices can be used. For example sutures, barbed sutures, staples or the like can be used to fasten the ligament in a retracted position that reduces stenosis.

Using the percutaneous methods and devices described herein, significant reductions of stenosis can be achieved. For example, a dural sac cross-sectional area less than 100 $mm^2$ or an anteroposterior (A-P) dimension of the canal of less than 10-12 mm in an average male is typically considered relative spinal stenosis. A dural sac cross-sectional area less than 85 $mm^2$ in an average male is considered severe spinal stenosis. The present devices and techniques are anticipated to cause an increase in canal area of 25 $mm^2$ per anchor or 50 $mm^2$ total. With resection and/or retraction of the ligamentum flavum, the cross-sectional area of the dural sac can be increased by 10 $mm^2$, and in some instances by as much as 20 $mm^2$ or even 30 $mm^2$ Likewise, the present invention can result in an increase of the anteroposterior dimension of the canal by 1 to 2 mm and in some instances by as much as 4 or 6 mm. The actual amount by which the cross-sectional area of the dural sac and/or the anteroposterior dimension of the canal are increased will depend on the size and age of the patient and the degree of stenosis and can be adjusted by the degree of retraction of the ligament.

Dural Shield

In some embodiments (not shown), a mechanical device such as a balloon or mechanical shield can also be used to create a protective guard or barrier between the borders of the epidural space and the adjacent structures. In one embodiment a durable expandable device is attached to the outside of the percutaneous laminectomy device, preferably on the side opposite the cutting aperture. The cutting device is inserted into the ligamentum flavum with the expandable device deflated. With the aperture directed away from the spinal canal, the expandable device is gently expanded via mechanical means or inflated with air or another sterile fluid, such as saline solution, via a lumen that may be within of, adjacent to the body of the device. This pushes the adjacent vital structures clear from the cutting aperture of the device and simultaneously presses the cutting aperture into the ligament. As above, the grasping and cutting needles can then be deployed and operated as desired. The balloon does not interfere with tissue excision because it is located on the side opposite the cutting aperture. The cutting needle may be hemispherical (semi-tubular) in shape with either a straight cutting or a sawing/reciprocating blade or may be sized to be placed within the outer housing that separates the balloon from the cutting aperture.

In another embodiment, a self-expanding metal mesh is positioned percutaneously in the epidural spaces. First the epidural space is accessed in the usual fashion. Then a guide catheter is placed in the epidural space at the site of the intended surgical procedure. The mesh is preferably compressed within a guide catheter. When the outer cover of the guide catheter is retracted, the mesh expands in the epidural space, protecting and displacing the adjacent dural sheath The mesh may be configured to have an expanded shape that generally corresponds to the shape of the desired safety zone within the spinal canal. At the conclusion of the surgical procedure, the mesh is pulled back into the guide sheath and the assembly removed. The mesh is deformable and compresses as it is pulled back into the guide catheter, in a manner similar to a self-expanding mesh stent. While there are commercially available self-expanding stents approved and in use in other applications, using a self-expandable mesh configured to expand within the epidural space so as to protect and displace the dural sac is novel.

The ipsilateral approach to the minimally invasive ligament decompression procedure methods, techniques, and devices described herein allow spinal decompression to be performed percutaneously, avoiding the pain, lengthy recovery time, and risk associated with open surgery. In addition, the ipsilateral approach to the minimally invasive ligament decompression procedure methods, techniques, and devices described herein permit clearer, less obstructed imaging views of the interlaminar spaces and ligamentum flavum between the laminae in the areas of interest. Such improved imaging views offer the potential for enhanced accuracy and safety in the placement of tools within the ligamentum flavum proximal the epidural space and spinal cord. Further, the ipsilateral approach to the minimally invasive ligament decompression procedure methods, techniques, and devices described herein permit the excision of portions of the ligaments flavum on the same lateral side of the median plane as that into which instruments and tools for the procedure are inserted.

Through the provision of a safety zone and improved imaging, the present devices and techniques offer reduced risk of spinal cord damage. In addition to improving nerve function, it is expected that decompression of the spinal canal in the manner described herein will result in improved blood flow to the neural elements by reducing the extrinsic pressure on the spinal vasculature. For these reasons, it is believed that spinal decompression performed according to the present invention will be preferable to decompression operations performed using currently known techniques.

While preferred embodiments of this invention have been shown and described, modifications thereof can be made by one skilled in the art without departing from the scope or teaching of this invention. For example, the means by which the safety zone is formed may be varied, the shape and configuration of the tissue excision devices may be varied, and the steps used in carrying out the technique may be modified. Accordingly, the invention is not limited to the embodiments described herein, but is only limited by the claims that follow, the scope of which shall include all equivalents of the subject matter of the claims Likewise, the sequential recitation of steps in a claim, unless explicitly so stated, is not intended to require that the steps be performed in any particular order or that a particular step be completed before commencement of another step.

What is claimed is:

1. A method for treating stenosis in a spine of a patient having a median plane, the spine including a spinal canal having a posterior surface, a dural sac and an epidural space between the posterior surface and dural sac, the location of the stenosis determining a region of interest in the spine, comprising the steps of:
   a) generating at least one view of a portion of the spinal canal in the region of interest;
   b) compressing the dural sac in the region of interest by injecting a fluid to form a safety zone and establish a working zone in the region of interest, the safety zone lying generally between the working zone and the dural sac;
   c) percutaneously accessing the region of interest on a first lateral side of the median plane via a tool trajectory that passes generally between a lamina of a superior first vertebra and a lamina of an inferior second vertebra and generally between the two superior articular processes of the inferior second vertebra, wherein the first and second vertebra are adjacent;
   d) inserting a tissue removal tool into tissue in the working zone on the first lateral side of the median plane via the tool trajectory;
   e) using the tissue removal tool to percutaneously reduce the stenosis on the first lateral side of the median plane; and
   f) utilizing the at least one view to position the tissue removal tool during at least a part of step d) and at least part of step e).

2. The method of claim 1 wherein a portion of a ligamentum flavum occupies the working zone in the region of interest, and wherein step e) comprises inserting the tissue removal tool into the ligamentum flavum in the region of interest and removing at least a portion of the ligamentum flavum in the region of interest.

3. The method of claim 2, wherein the ligamentum flavum in the region of interest has an anterior surface extending into the spinal canal and a posterior surface distal the spinal canal and wherein portions of the ligamentum flavum are first removed from the ligamentum flavum proximal to the anterior surface.

4. The method of claim 1 wherein said at least one view is a caudal-cranial posterior view.

5. The method of claim 1 wherein said at least one view is a caudal-cranial posterior-lateral view.

6. The method of claim 4 wherein the patient has an anterior front surface and a posterior back surface, and wherein the caudal-cranial posterior view is generated by positioning an imaging device at an angle $\Theta$ relative to the posterior back surface, wherein $\Theta$ is between 50 and 80 degrees.

7. The method of claim 5 wherein the patient has an anterior front surface and a posterior back surface, and wherein the caudal-cranial posterior-lateral view is generated by positioning an imaging device at an angle $\Theta$ relative to the posterior back surface and positioning the imaging device lateral to the spine, wherein $\Theta$ is between 50 and 80 degrees.

8. The method of claim 1, further comprising utilizing a caudal-cranial posterior view and a caudal-cranial posterior-lateral view to perform at least part of steps d) and e).

9. A method of accessing a spinal location of a patient wherein the patient has a posterior back surface and wherein the method comprises:
   a) positioning an instrument against the posterior back surface, wherein the instrument is positioned for insertion in a generally superior direction and is positioned at an initial angle relative to a generally longitudinal axis of the patient's spine, wherein the initial angle is less than about 20 degrees;
   b) inserting the instrument into the posterior back surface of the patient generally toward a region of interest, wherein the region of interest includes a working zone;
   c) advancing the instrument towards the region of interest along an ipsilateral trajectory that passes generally between a lamina of a superior first vertebra and a lamina of an inferior second vertebra and generally between the two superior articular processes of the inferior second vertebra, wherein the first and second vertebra are adjacent;
d) inserting the instrument into the working zone; and
e) removing tissue from the working zone.

10. The method of claim 9 wherein the instrument is initially inserted into the posterior back surface of the patient between about 5 and about 10 cm inferior to the region of interest.

11. The method of claim 9 wherein the instrument is adjustable to an angle .theta. that is between about 0 and about 90 degrees relative to the posterior back surface.

12. The method of claim 9, wherein the instrument comprises a cannula having a central bore configured to receive a tissue removal tool.

13. The method of claim 9, wherein the instrument is a tissue removal tool configured to remove tissue from the working zone.

14. The method of claim 1 wherein step e) comprises:
e1) engaging a tissue sample in the working zone with the tissue removal tool;
e2) excising the tissue sample with the tissue removal tool;
e3) removing the tissue sample from the working zone with the tissue removal tool; and
e4) repeating steps e1) through e3) until a desired amount of tissue has been removed.

15. The method of claim 14 wherein the tissue sample comprises tissue selected from the group consisting of the ligamentum flavum, fat, and bone.

16. The method of claim 14 wherein step e3 is carried out without repositioning the tissue removal tool in the tissue.

17. The method of claim 1 wherein the injected fluid includes a contrast medium.

18. The method of claim 1 wherein the injected fluid has a temperature-dependent viscosity and is more viscous at 37° C. than at 30° C.

19. The method of claim 9, wherein fluoroscopic imaging is used during at least one of step c) and d).

* * * * *

UNITED STATES PATENT AND TRADEMARK OFFICE
CERTIFICATE OF CORRECTION

| | | |
|---|---|---|
| PATENT NO. | : 7,942,830 B2 | Page 1 of 1 |
| APPLICATION NO. | : 11/382349 | |
| DATED | : May 17, 2011 | |
| INVENTOR(S) | : Murray David Solsberg et al. | |

It is certified that error appears in the above-identified patent and that said Letters Patent is hereby corrected as shown below:

Claim 11, col. 21, line 11, "an angle .theta." should read --an angle $\Theta$--

Signed and Sealed this
Twenty-ninth Day of May, 2012

David J. Kappos
*Director of the United States Patent and Trademark Office*